(12) United States Patent
Anderson et al.

(10) Patent No.: US 10,556,118 B2
(45) Date of Patent: *Feb. 11, 2020

(54) EXTRA-CARDIOVASCULAR PACING BY AN IMPLANTABLE CARDIOVERTER DEFIBRILLATOR

(71) Applicant: Medtronic, Inc., Minneapolis, MN (US)

(72) Inventors: David A. Anderson, Stanchfield, MN (US); Mark T. Marshall, Forest Lake, MN (US); Vladimir P. Nikolski, Blaine, MN (US); Robert T. Sawchuk, Roseville, MN (US); Amy E. Thompson-Nauman, Ham Lake, MN (US); John D. Wahlstrand, Shoreview, MN (US); Gregory A. Younker, White Bear Township, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/132,564

(22) Filed: Sep. 17, 2018

(65) Prior Publication Data

US 2019/0015671 A1 Jan. 17, 2019

Related U.S. Application Data

(63) Continuation of application No. 15/367,516, filed on Dec. 2, 2016, now Pat. No. 10,080,905.

(Continued)

(51) Int. Cl.
*A61N 1/39* (2006.01)
*A61N 1/37* (2006.01)
(Continued)

(52) U.S. Cl.
CPC ......... *A61N 1/3962* (2013.01); *A61N 1/3621* (2013.01); *A61N 1/371* (2013.01);
(Continued)

(58) Field of Classification Search
CPC ... A61N 1/3712; A61N 1/3962; A61N 1/3987
See application file for complete search history.

(56) References Cited

U.S. PATENT DOCUMENTS 5,184,616 A 2/1993 Weiss
5,215,083 A 6/1993 Drane
(Continued)

FOREIGN PATENT DOCUMENTS

EP 2376193 B1 3/2014
WO 9316757 A1 9/1993
(Continued)

OTHER PUBLICATIONS (PCT/US2016/064582) PCT Notification of Transmittal of the International Search Report and the Written Opinion of the International Searching Authority, dated Mar. 17, 2017, 14 pages.
(Continued)

*Primary Examiner* — William J Levicky

(57) ABSTRACT

An extra-cardiovascular implantable cardioverter defibrillator (ICD) having a low voltage therapy module and a high voltage therapy module is configured to select, by a control module of the ICD, a pacing output configuration from at least a low-voltage pacing output configuration of the low voltage therapy module and a high-voltage pacing output configuration of the high voltage therapy module. The high voltage therapy module includes a high voltage capacitor having a first capacitance and the low voltage therapy module includes a plurality of low voltage capacitors each having up to a second capacitance that is less than the first capacitance. The ICD control module controls a respective
(Continued)

one of the low voltage therapy module or the high voltage therapy module to deliver extra-cardiovascular pacing pulses in the selected pacing output configuration via extra-cardiovascular electrodes coupled to the ICD.

20 Claims, 15 Drawing Sheets

Related U.S. Application Data

(60) Provisional application No. 62/262,499, filed on Dec. 3, 2015.

(51) Int. Cl.
    *A61N 1/362*     (2006.01)
    *A61N 1/375*     (2006.01)
    *A61N 1/05*     (2006.01)

(52) U.S. Cl.
    CPC ......... *A61N 1/3706* (2013.01); *A61N 1/3712* (2013.01); *A61N 1/3758* (2013.01); *A61N 1/3925* (2013.01); *A61N 1/3987* (2013.01); *A61N 1/0587* (2013.01)

(56) References Cited

U.S. PATENT DOCUMENTS

| | | | |
|---|---|---|---|
| 5,824,018 A | 10/1998 | Dreher | |
| 6,778,860 B2 | 8/2004 | Ostroff | |
| 6,856,835 B2 | 2/2005 | Bardy | |
| 6,865,417 B2 | 3/2005 | Rissmann | |
| 6,952,608 B2 | 10/2005 | Ostroff | |
| 6,952,610 B2 | 10/2005 | Ostroff | |
| 6,954,670 B2 | 10/2005 | Ostroff | |
| 7,092,754 B2 | 8/2006 | Bardy | |
| 7,146,212 B2 | 12/2006 | Bardy | |
| 7,184,833 B2 | 2/2007 | Ganion | |
| 7,389,139 B2 | 6/2008 | Ostroff | |
| 7,392,081 B2 | 6/2008 | Wagner | |
| 7,471,983 B2 | 12/2008 | Voegele | |
| 7,502,645 B2 | 3/2009 | Ostroff | |
| 7,522,957 B2 | 4/2009 | Ostroff | |
| 7,751,885 B2 | 7/2010 | Bardy | |
| 7,761,150 B2 | 7/2010 | Ghanem | |
| 8,036,742 B2 | 10/2011 | Sullivan | |
| 8,155,740 B2 | 4/2012 | Wanasek | |
| 8,195,291 B2 | 6/2012 | Norton | |
| 8,359,094 B2 | 1/2013 | Bonner | |
| 8,412,320 B2 | 4/2013 | Ostroff | |
| 8,452,399 B2 | 5/2013 | Wanasek | |
| 8,758,365 B2 | 6/2014 | Bonner | |
| 8,914,105 B2 | 12/2014 | Wanasek | |
| 2008/0183230 A1 | 7/2008 | Kemmetmueller | |
| 2008/0275531 A1 | 11/2008 | Bulkes | |
| 2009/0210021 A1 | 8/2009 | Ostroff | |
| 2012/0197330 A1 | 8/2012 | Crutchfield | |
| 2014/0330328 A1* | 11/2014 | Christie | A61N 1/3962 607/4 |
| 2015/0300375 A1 | 10/2015 | Begon | |
| 2015/0306410 A1 | 10/2015 | Marshall | |
| 2016/0158567 A1 | 6/2016 | Marshall | |
| 2017/0157399 A1 | 6/2017 | Anderson | |
| 2017/0157412 A1 | 6/2017 | Nikolski | |

FOREIGN PATENT DOCUMENTS

| | | |
|---|---|---|
| WO | 9958192 A1 | 11/1999 |
| WO | 2006115940 A1 | 11/2006 |
| WO | 2010088355 A1 | 8/2010 |
| WO | 2015164442 A1 | 10/2015 |
| WO | 2015164473 A1 | 10/2015 |

OTHER PUBLICATIONS (PCT/US2016/064646) PCT Notification of Transmittal of the International Search Report and the Written Opinion of the International Searching Authority, dated Mar. 17, 2017, 10 pages.

\* cited by examiner

EXTRA-CARDIOVASCULAR PACING BY AN IMPLANTABLE CARDIOVERTER DEFIBRILLATOR

REFERENCE TO RELATED APPLICATION

This application is a Continuation of U.S. patent application Ser. No. 15/367,516, filed Dec. 2, 2016, entitled "EXTRA-CARDIOVASCULAR PACING BY AN IMPLANTABLE CARDIOVERTER DEFIBRILLATOR," which claims the benefit of U.S. Patent Application Ser. No. 62/262,499, filed provisionally on Dec. 3, 2015, entitled "EXTRA-CARDIOVASCULAR PACING USING HIGH-VOLTAGE THERAPY CIRCUITRY OF AN IMPLANTABLE CARDIOVERTER DEFIBRILLATOR," the content of both of which is incorporated herein by reference in their entirety.

TECHNICAL FIELD

The disclosure relates generally to an extra-cardiovascular implantable cardioverter defibrillator (ICD) system, device and method for delivering cardiac pacing pulses using extra-cardiovascular electrodes.

BACKGROUND

Medical devices, such as cardiac pacemakers and ICDs, provide therapeutic electrical stimulation to a heart of a patient via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart. For example, an ICD may deliver pacing pulses to the heart of the patient upon detecting bradycardia or tachycardia or deliver cardioversion or defibrillation shocks to the heart upon detecting tachycardia or fibrillation.

SUMMARY

In general, the disclosure is directed to techniques for delivering cardiac pacing pulses to a patient's heart by a cardiac defibrillation system, such as an extra-cardiovascular ICD system. An ICD operating according to the techniques disclosed herein delivers cardiac pacing pulses using extra-cardiovascular electrodes carried by a medical electrical lead extending from the ICD. The ICD includes both a high voltage therapy module and a low voltage therapy module and is configured to automatically determine a pacing output configuration using either the high voltage therapy module or the low voltage therapy module and a selected extra-cardiovascular pacing electrode vector. In some examples, one or more low-voltage, pacing output configurations are available from the low voltage therapy module including a low-voltage pacing output configuration for delivering single-pulse pacing pulses and/or a low-voltage pacing output configuration for delivering composite pacing pulses that include two or more individual pulses delivered within the composite pacing pulse width to evoke a single cardiac depolarization.

In one example, the disclosure provides an extra-cardiovascular ICD including a high voltage therapy module, a low voltage therapy module, and a control module. The high voltage therapy module includes a high voltage capacitor having a first capacitance, a high voltage charging circuit configured to charge the high voltage capacitor, and switching circuitry configured to couple the high voltage capacitor across extra-cardiovascular electrodes coupled to the ICD. The low voltage therapy module includes multiple low voltage capacitors each having a capacitance up to a second capacitance that is less than the first capacitance, a low voltage charging circuit configured to charge the low voltage capacitors, and switching circuitry configured to selectively couple the plurality of low voltage capacitors to the extra-cardiovascular electrodes. The control module is coupled to the high voltage therapy module and the low voltage therapy module and is configured to select a pacing output configuration from among at least a low-voltage pacing output configuration of the low voltage therapy module and a high-voltage pacing output configuration of the high voltage therapy module and control a respective one of the low voltage therapy module or the high voltage therapy module to deliver extra-cardiovascular pacing pulses by the selected one of the low-voltage pacing output configuration or the high-voltage pacing output configuration via the extra-cardiovascular electrodes coupled to the ICD.

In another example, the disclosure provides a method performed by an extra-cardiovascular ICD having a low voltage therapy module and a high voltage therapy module. The method includes selecting by a control module of the ICD a pacing output configuration from among at least a low-voltage, pacing output configuration of the low voltage therapy module and a high-voltage, pacing output configuration of the high voltage therapy module. The high voltage therapy module includes a high voltage capacitor having a first capacitance, and the low voltage therapy module includes multiple low voltage capacitors each having up to a second capacitance that is less than the first capacitance. The method further includes controlling a respective one of the low voltage therapy module or the high voltage therapy module to deliver extra-cardiovascular pacing pulses in the selected one of the low-voltage pacing output configuration or the high-voltage pacing output configuration via extra-cardiovascular electrodes coupled to the ICD.

In another example, the disclosure provides a non-transitory, computer-readable storage medium storing a set of instructions which, when executed by a control module of an extra-cardiovascular ICD having a low voltage therapy module and a high voltage therapy module, cause the ICD to select a pacing output configuration from among a low-voltage pacing output configuration of the low voltage therapy module and a high-voltage pacing output configuration of the high voltage therapy module. The high voltage therapy module includes a high voltage capacitor having a first capacitance, and the low voltage therapy module includes multiple low voltage capacitors each having up to a second capacitance that is less than the first capacitance. The ICD is further caused to control a respective one of the low voltage therapy module or the high voltage therapy module to deliver extra-cardiovascular pacing pulses in the selected one of the low-voltage pacing output configuration or the high-voltage pacing output configuration via extra-cardiovascular electrodes coupled to the ICD.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for delivering cardiac pacing pulses using implanted, extra-cardiovascular electrodes. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The techniques disclosed herein provide a method for automatically configuring an ICD pacing output configuration using extra-cardiovascular electrodes.

Figure 1A:
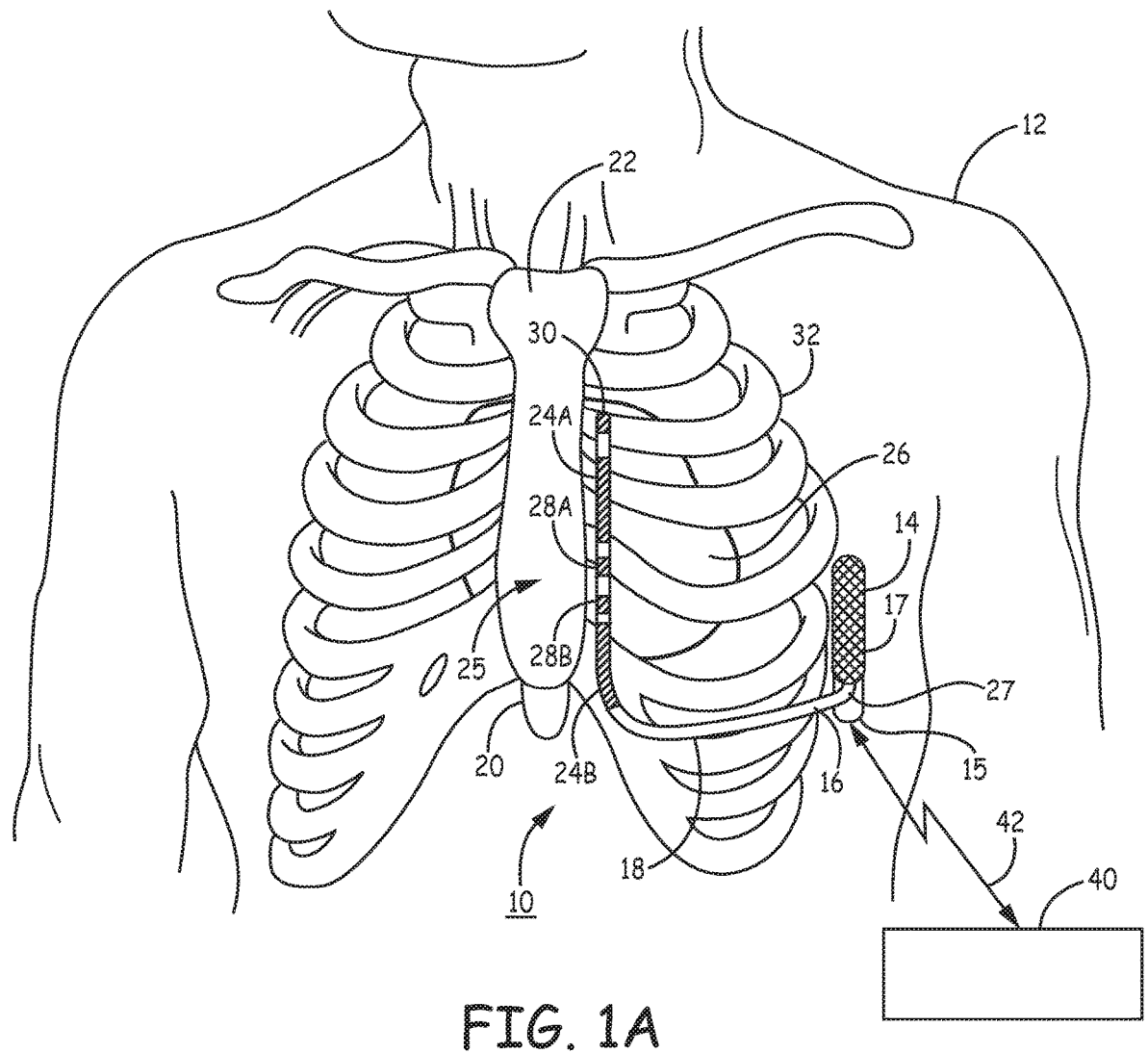
FIGS. 1A and 1B are conceptual diagrams of an extra-cardiovascular ICD system according to one example.
Figure 1B:
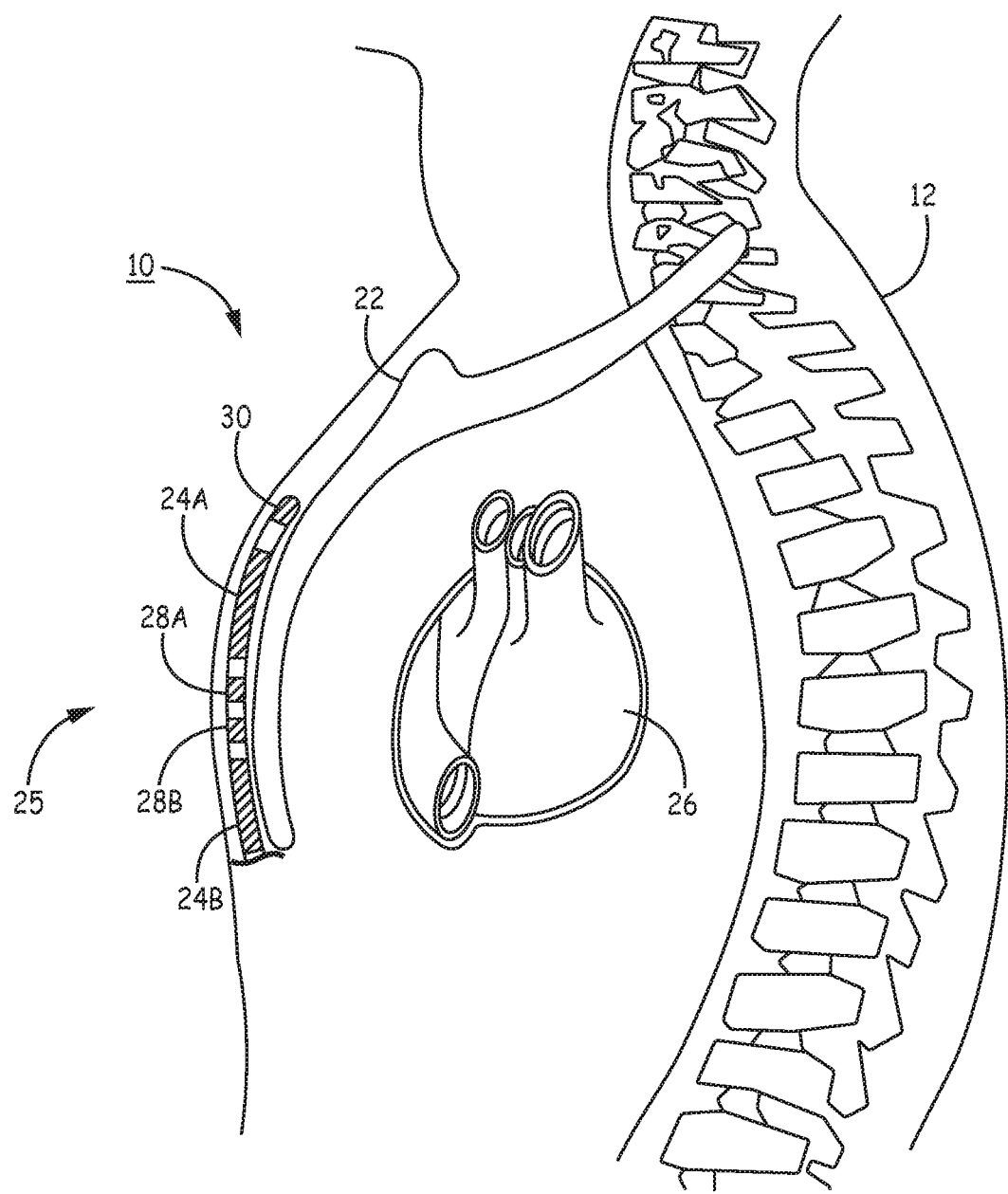

FIGS. 1A and 1B are conceptual diagrams of an extra-cardiovascular ICD system 10 according to one example. FIG. 1A is a front view of ICD system 10 implanted within patient 12. FIG. 1B is a side view of a portion of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and cardiac pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as a housing electrode (sometimes referred to as a "can" electrode). In examples described herein, housing 15 may be used as an active can electrode for use in delivering cardioversion/defibrillation (CV/DF) shocks or other high voltage pulses delivered using a high voltage therapy module. In other examples, housing 15 may be available for use in delivering unipolar, low voltage cardiac pacing pulses in conjunction with lead-based electrodes. In other instances, the housing 15 of ICD 14 may include a plurality of electrodes on an outer portion of the housing. The outer portion(s) of the housing 15 functioning as an electrode(s) may be coated with a material, such as titanium nitride.

ICD 14 includes a connector assembly 17 (also referred to as a connector block or header) that includes electrical feedthroughs crossing housing 15 to provide electrical connections between conductors extending within an elongated lead body 18 of lead 16 and electronic components included within the housing 15 of ICD 14. As will be described in further detail herein, housing 15 may house one or more processors, memories, transceivers, sensors, electrical sensing circuitry, therapy delivery circuitry, power sources and other appropriate components.

Elongated lead body 18 includes a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead 16 includes defibrillation electrodes 24A and 24B, collectively 24, and pace/sense electrodes 28A, 28B, and 30. In some cases, defibrillation electrodes 24A and 24B may together form a defibrillation electrode in that they are configured to be activated concurrently. Alternatively, defibrillation electrodes 24A and 24B may form separate defibrillation electrodes in which case each of the electrodes 24A and 24B may be activated independently. In some instances, defibrillation electrodes 24A and 24B are coupled to electrically isolated conductors, and ICD 14 may include switching mechanisms to allow electrodes 24A and 24B to be utilized as a single defibrillation electrode (e.g., activated concurrently to form a common cathode or anode) or as separate defibrillation electrodes, (e.g., activated individually, one as a cathode and one as an anode or activated one at a time, one as an anode or cathode and the other remaining inactive with housing 15 as an active electrode).

Electrodes 24A and 24B (and in some example housing 15) are referred to as defibrillation electrodes because they are utilized, individually or collectively, for delivering high voltage stimulation therapy (e.g., cardioversion or defibrillation shocks). Electrodes 24A and 24B may be elongated coil electrodes and generally have a relatively high surface area for delivering high voltage electrical stimulation pulses compared to low voltage pacing and sensing electrodes. However, electrodes 24A and 24B and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24A and 24B to use in only high voltage cardioversion/defibrillation therapy applications. As described herein, electrodes 24A and/or 24B may be used in a pacing electrode vector for delivering extra-cardiovascular pacing pulses using a high-voltage, pacing output configuration.

Electrodes 28A, 28B and 30 are relatively smaller surface area electrodes for delivering low voltage pacing pulses and for sensing cardiac electrical signals. Electrodes 28A, 28B and 30 are referred to as pace/sense electrodes because they are generally configured for use in low voltage applications, e.g., used as either a cathode or anode for delivery of pacing pulses and/or sensing of cardiac electrical signals. In some instances, electrodes 28A, 28B, and 30 may provide only pacing functionality, only sensing functionality or both.

In the example illustrated in FIGS. 1A and 1B, electrodes 28A and 28B are located between defibrillation electrodes 24A and 24B and electrode 30 is located distal to defibrillation electrode segment 24A. Electrodes 28A and 28B are illustrated as ring electrodes, and electrode 30 is illustrated as a hemispherical tip electrode in the example of FIGS. 1A and 1B. However, electrodes 28A, 28B, and 30 may comprise any of a number of different types of electrodes, including ring electrodes, short coil electrodes, paddle electrodes, hemispherical electrodes, directional electrodes, segmented electrodes, or the like, and may be positioned at any position along the distal portion 25 of lead 16. Further, electrodes 28A, 28B, and 30 may be of similar type, shape, size and material or may differ from each other.

Lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIGS. 1A and 1B as being offset laterally from and extending substantially parallel to sternum 22, lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of lead 16 may depend on the location of ICD 14 or other factors.

Electrical conductors (not illustrated) extend through one or more lumens of the elongated lead body 18 of lead 16 from the lead connector at the proximal lead end 27 to electrodes 24A, 24B, 28A, 28B, and 30 located along the distal portion 25 of the lead body 18. Lead body 18 may be tubular or cylindrical in shape. In other examples, the distal portion 25 (or all of) the elongated lead body 18 may have a flat, ribbon or paddle shape.

The lead body 18 of lead 16 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The elongated electrical conductors contained within the lead body 18 are each electrically coupled with respective defibrillation electrodes 24A and 24B and pace/sense electrodes 28A, 28B, and 30. The respective conductors electrically couple the electrodes 24A, 24B, 28A, 28B and 30 to circuitry, such as a therapy module and/or a sensing module, of ICD 14 via connections in the connector assembly 17, including associated electrical feedthroughs crossing housing 15. The electrical conductors transmit therapy from a therapy module within ICD 14 to one or more of defibrillation electrodes 24A and 24B and/or pace/sense electrodes 28A, 28B, and 30 and transmit sensed electrical signals from one or more of defibrillation electrodes 24A and 24B and/or pace/sense electrodes 28A, 28B, and 30 to the sensing module within ICD 14.

FIGS. 1A and 1B are illustrative in nature and should not be considered limiting of the practice of the techniques disclosed herein. In other examples, lead 16 may include less than three pace/sense electrodes or more than three pace/sense electrodes and/or a single defibrillation electrode or more than two electrically isolated or electrically coupled defibrillation electrodes or electrode segments. The pace/sense electrodes 28A, 28B, and 30 may be located elsewhere along the length of lead 16, e.g., distal to defibrillation electrode 24A, proximal to defibrillation electrode 24B, and/or between electrodes 24A and 24B. For example, lead 16 may include a single pace/sense electrode 28 between defibrillation electrodes 24A and 24B and no pace/sense electrode distal to defibrillation electrode 24A or proximal to defibrillation electrode 24B.

In other examples, lead 16 may include only a single pace/sense electrode 28 between defibrillation electrodes 24A and 24B and include another discrete electrode(s) distal to defibrillation electrode 24A and/or proximal to defibrillation electrode segment 24B. Various example configurations of extra-cardiovascular leads and electrodes and dimensions that may be implemented in conjunction with the extra-cardiovascular pacing techniques disclosed herein are described in commonly-assigned U.S. Pat. Publication No. 2015/0306375 (Marshall, et al.) and U.S. Pat. Publication No. 2015/0306410 (Marshall, et al.), both of which are incorporated herein by reference in their entirety.

In still other examples, ICD system 10 of FIGS. 1A and 1B may include a second extra-cardiovascular electrical stimulation and sensing lead similar to lead 16. The second lead may, for example, extend laterally to the posterior of patient 12 and include one or more electrodes that form an electrode vector with one or more of electrodes 24A, 24B, 28A, 28B, and/or 30 of lead 16 for providing pacing in accordance with the techniques disclosed herein.

In some instances, electrodes 24A, 24B, 28A, 28B, and/or 30 of lead 16 may be shaped, oriented, designed or otherwise configured to reduce extra-cardiac stimulation. For example, electrodes 24A, 24B, 28A, 28B, and/or 30 of lead 16 may be shaped, oriented, designed, partially insulated or otherwise configured to focus, direct or point electrodes 24A, 24B, 28A, 28B, and/or 30 toward heart 26. In this manner, electrical stimulation pulses delivered via lead 16 are directed toward heart 26 and not outward toward skeletal muscle. For example, electrodes 24A, 24B, 28A, 28B, and/or 30 of lead 16 may be partially coated or masked with a polymer (e.g., polyurethane) or another coating material (e.g., tantalum pentoxide) on one side or in different regions so as to direct the electrical energy toward heart 26 and not outward toward skeletal muscle. In the case of a ring electrode, for example, the ring electrode may be partially coated with the polymer or other material to form a half-ring electrode, quarter-ring electrode, or other partial-ring electrode. When ICD 14 delivers pacing pulses via electrodes 24A, 24B, 28A, 28B, and/or 30, recruitment of surrounding skeletal muscle by the pacing pulses, which can cause discomfort to the patient, may be reduced by shaping, orienting, or partially insulating electrodes 24 to focus or direct electrical energy toward heart 26.

ICD 14 may obtain electrical signals corresponding to electrical activity of heart 26 via a combination of sensing vectors that include combinations of electrodes 28A, 28B, and 30 and the housing 15 of ICD 14. For example, ICD 14 may obtain cardiac electrical signals sensed using a sensing vector between combinations of electrodes 28A, 28B, and 30 with one another or obtain cardiac electrical signals using a sensing vector between any one or more of electrodes 28A, 28B, and 30 and the conductive housing 15 of ICD 14. In some instances, ICD 14 may even obtain cardiac electrical signals using a sensing vector that includes one or both defibrillation electrodes 24A or 24B such as between each other or in combination with one or more of electrodes 28A, 28B, and 30, and/or the housing 15.

ICD 14 analyzes the cardiac electrical signals received from one or more of the sensing vectors to monitor for abnormal rhythms, such as bradycardia, ventricular tachycardia (VT) or ventricular fibrillation (VF). ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated by reference herein in its entirety.

ICD 14 generates and delivers electrical stimulation therapy in response to detecting a tachyarrhythmia (e.g., VT or VF). ICD 14 may deliver one or more cardioversion or defibrillation shocks via one or both of defibrillation electrodes 24A and 24B and/or housing 15. ICD 14 may deliver the cardioversion or defibrillation shocks using electrodes 24A and 24B individually or together as a cathode (or anode) and with the housing 15 as an anode (or cathode).

ICD 14 may generate and deliver electrical stimulation pulses other than cardioversion or defibrillation shocks, including bradycardia pacing pulses, anti-tachycardia pacing (ATP) pulses, pacing pulses during asystole due to atrioventricular conduction block or post-shock, burst delivery for VF induction, and/or entrainment pacing pulses before a T-shock for VF induction using a therapy vector formed from one or more of any of a variety of electrode vectors that include one or more of the electrodes 24A, 24B, 28A, 28B and/or 30, and/or the housing 15 of ICD 14. As described below, ICD 14 may be configured to select a pacing output configuration using either a low voltage therapy module or a high voltage therapy module and a pacing electrode vector selected from among electrodes 24A, 24B, 28A, 28B, 30 and housing 15 for delivering a pacing therapy (e.g., ATP, asystole pacing post-shock or during atrioventricular conduction block, or bradycardia pacing) or for delivering a tachyarrhythmia induction sequence that includes entrainment pacing pulses prior to a T-shock or high frequency burst pulses (e.g., 50 Hz burst pulses). The methods disclosed herein for selecting a pacing output configuration may be used in conjunction with the tachyarrhythmia induction methods generally disclosed in provisional U.S. Patent Application 62/262,500 and corresponding U.S. Patent Application Publication No. 2017/0157412, filed on the same date herewith), both incorporated herein by reference in their entirety.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferior from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from ICD 14 and to program operating parameters and algorithms in ICD 14 for controlling ICD functions. External device 40 may be used to program cardiac rhythm detection parameters and therapy control parameters used by ICD 14. Control parameters used to generate and deliver cardiac electrical stimulation pulses according to techniques disclosed herein may be programmed into ICD 14 using external device 40.

Data stored or acquired by ICD 14, including physiological signals or associated data derived therefrom, results of device diagnostics, and histories of detected rhythm episodes and delivered therapies, may be retrieved from ICD 14 by external device 40 following an interrogation command. For example, pacing capture threshold tests may be initiated by a user interacting with external device 40. A user may observe cardiac electrical signals retrieved from ICD 14 on a display of external device 40 for confirming cardiac capture by pacing pulses delivered by ICD 14 during a capture threshold test. External device 40 may alternatively be embodied as a home monitor or hand held device.

Figure 2A:
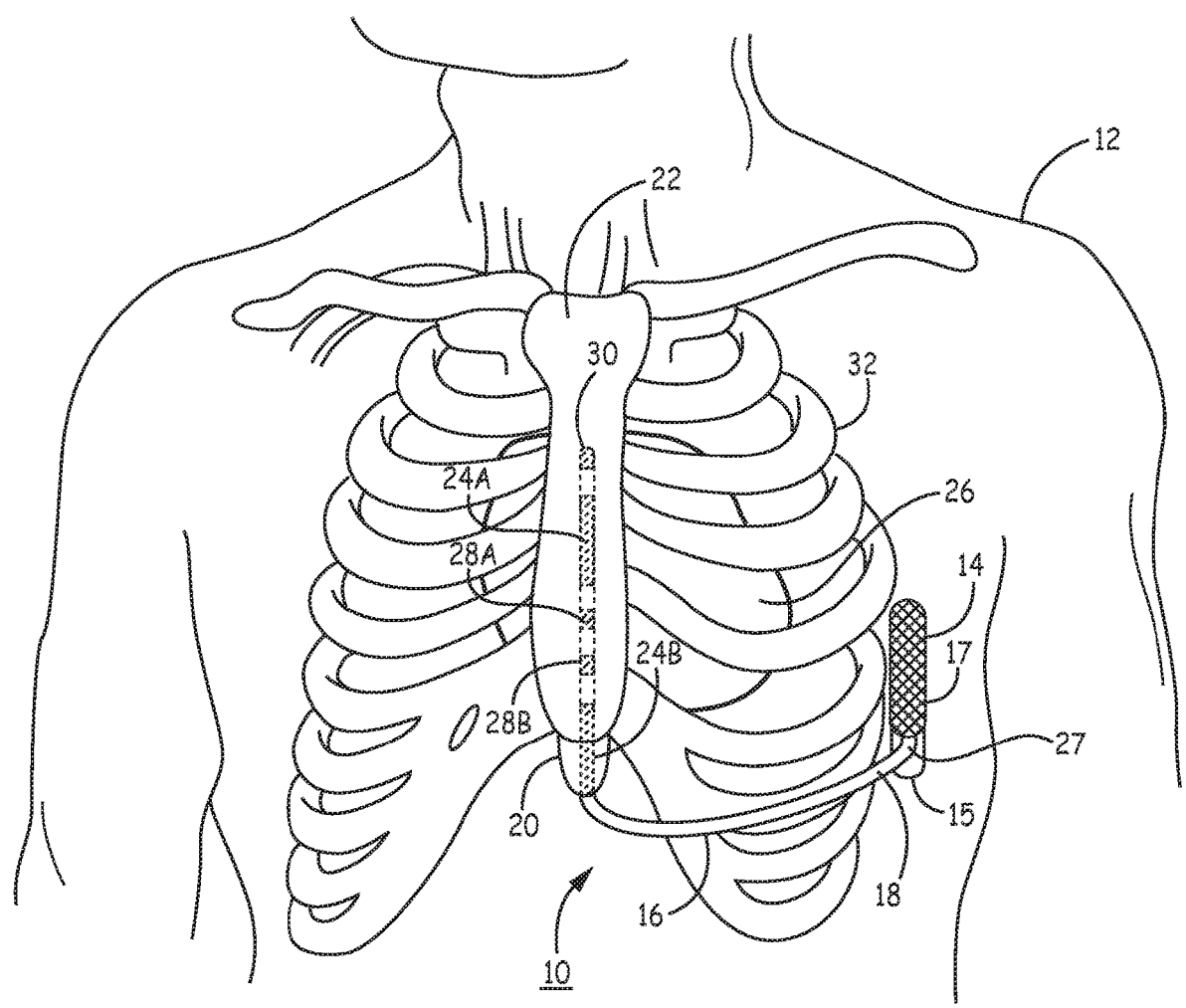
FIGS. 2A-2C are conceptual diagrams of a patient implanted with the extra-cardiovascular ICD system of FIG. 1A in a different implant configuration.
Figure 2B:
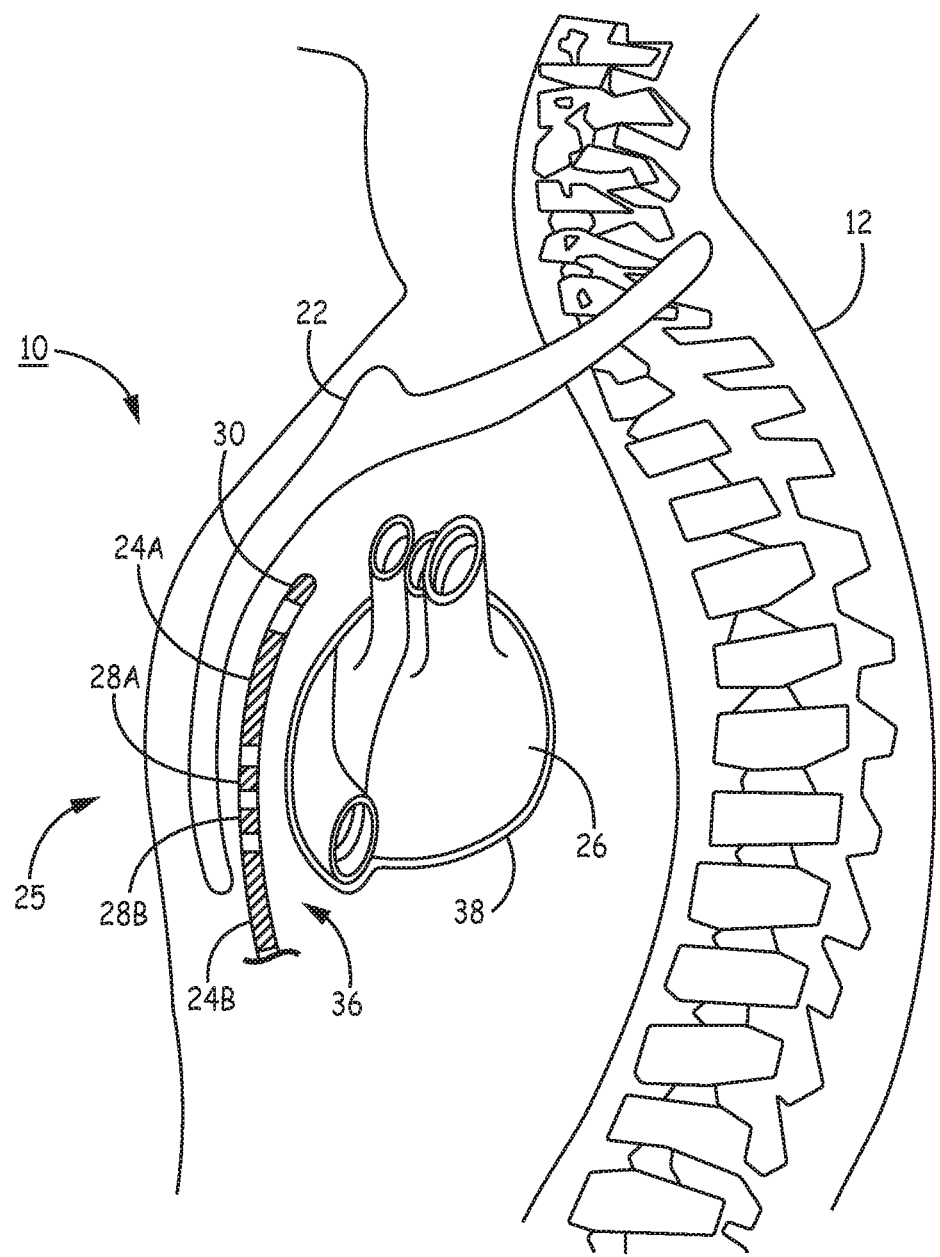
Figure 2C:
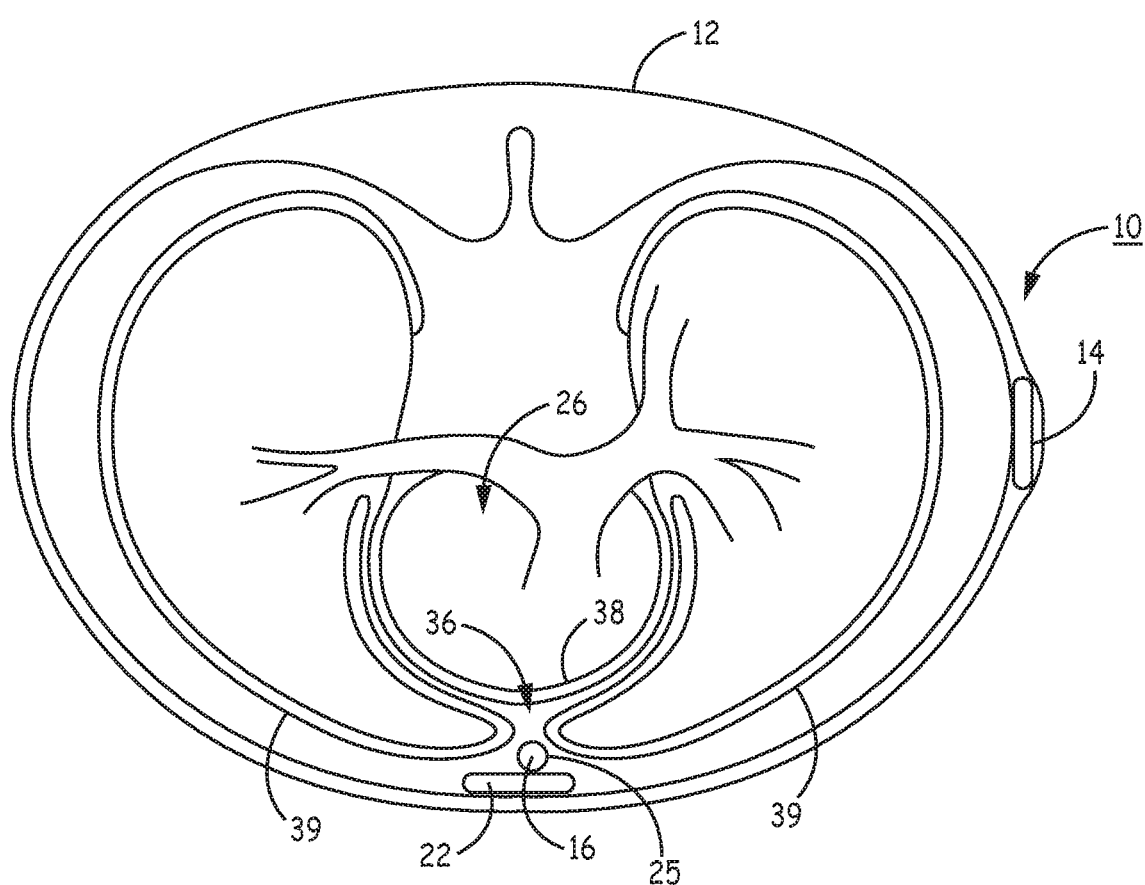

FIGS. 2A-2C are conceptual diagrams of patient 12 implanted with ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis muscle and one or more costal cartilages. Anterior mediastinum 36 includes a quantity of loose connective tissue (such as areolar tissue), adipose tissue, some lymph vessels, lymph glands, substernal musculature, small side branches of the internal thoracic artery or vein, and the thymus gland. In one example, the distal portion 25 of lead 16 extends along the posterior side of sternum 22 substantially within the loose connective tissue and/or substernal musculature of anterior mediastinum 36.

A lead implanted such that the distal portion 25 is substantially within anterior mediastinum 36 may be referred to as a "substernal lead." In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to but typically not within the pericardium 38 of heart 26. Other implant locations and lead and electrode arrangements that may be used in conjunction with the cardiac pacing techniques described herein are generally disclosed in the above-incorporated references. Although example extra-cardiovascular locations are described above with respect to FIGS. 1A, 1B and 2A-2C, the pacing techniques of this disclosure may be utilized in other implementations in which pacing amplitudes and/or widths associated with conventional intra-cardiac pacing pulses are insufficient to capture the patient's heart, including within the pericardial space.

Figure 3:
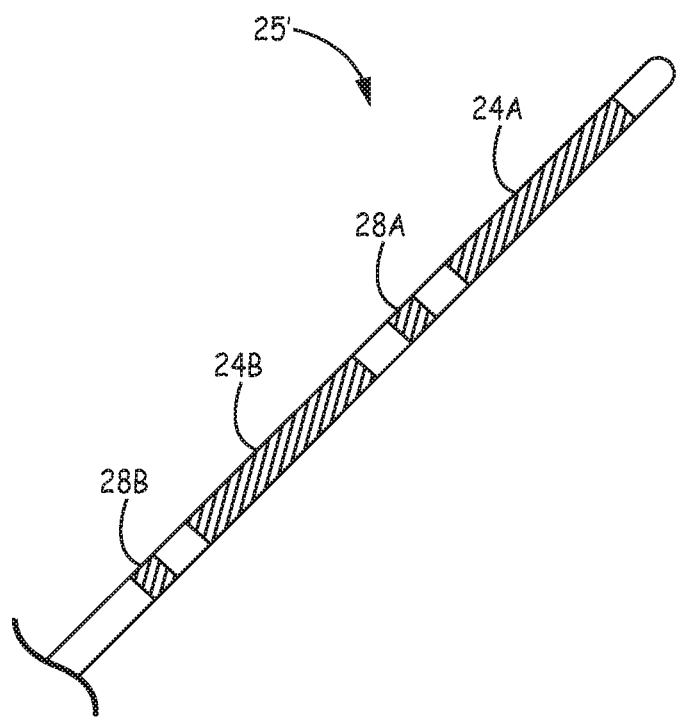
FIG. 3 is a conceptual diagram of a distal portion of an extra-cardiovascular lead having an electrode configuration according to another example.

FIG. 3 is a conceptual diagram illustrating a distal portion 25' of another example of implantable electrical lead 16 having an alternative electrode arrangement. In this example, distal portion 25' includes two pace/sense electrodes 28A and 28B and two defibrillation electrodes 24A and 24B and respective conductors (not shown) to provide the electrical stimulation and sensing functionality as described above in conjunction with FIGS. 1A, 1B and FIGS. 2A-2C. In this example, however, electrode 28B is proximal to proximal defibrillation electrode 24B, and electrode 28A is distal to proximal defibrillation electrode 24B such that electrodes 28A and 28B are separated by defibrillation electrode 24B. In a further example, in addition to electrodes 28A and 28B, lead 16 may include a third pace/sense electrode located distal to defibrillation electrode 24A.

The spacing and location of pace/sense electrodes 28A and 28B may be selected to provide pacing vectors that enable efficient pacing of heart 26. The lengths and spacing of electrodes 24A, 24B, 28A and 28B may correspond to any of the examples provided in the above-incorporated references. For example, the distal portion 25' of lead 16 from the distal end to the proximal side of the most proximal electrode (e.g., electrode 28B in the example of FIG. 3) may be less than or equal to 15 cm and may be less than or equal to 13 cm and or even less than or equal to 10 cm. The spacing and location of pace/sense electrodes 28A and 28B may be selected to provide pacing vectors that enable efficient pacing of heart 26. It is contemplated that one or more pace/sense electrodes may be distal to distal defibrillation electrode 24A, one or more pace/sense electrodes may be between defibrillation electrodes 24A and 24B, and/or one or more pace/sense electrodes may be proximal to proximal defibrillation electrode 24B. Having multiple pace/sense electrodes at different locations along lead body 18 enables selection from among a variety of inter-electrode spacings, which allows a pacing electrode pair (or combination) to be selected having an inter-electrode spacing that results in the greatest pacing efficiency.

ICD 14 may deliver electrical stimulation and/or sense electrical signals using any electrode vector that includes defibrillation electrodes 24A and 24B (individually or collectively), and/or electrodes 28A and/or 28B, and/or the housing 15 of ICD 14. For example, ICD 14 may deliver pacing pulses using a low voltage therapy module via a pacing electrode vector in which one of electrodes 28A or 28B is selected as a cathode and the other of electrodes 28A and 28B is selected as the anode. Other examples of low-voltage therapy delivery electrode vectors may include one of electrodes 28A or 28B or both in combination selected as a cathode (or anode) with one of defibrillation electrodes 24A, 24B or housing 15 selected as an anode (or cathode). ICD 14 may deliver pacing pulses using a high voltage therapy module using a pacing electrode vector that uses one or both of defibrillation electrodes 24A and 24B as a cathode (or anode) and the housing 15 of ICD 14 as an anode (or cathode). ICD 14 is configured to determine which pacing vector and which one of a low voltage therapy module and a high voltage therapy module are used to deliver cardiac pacing pulses, e.g., in accordance with the techniques described herein.

Figure 4:
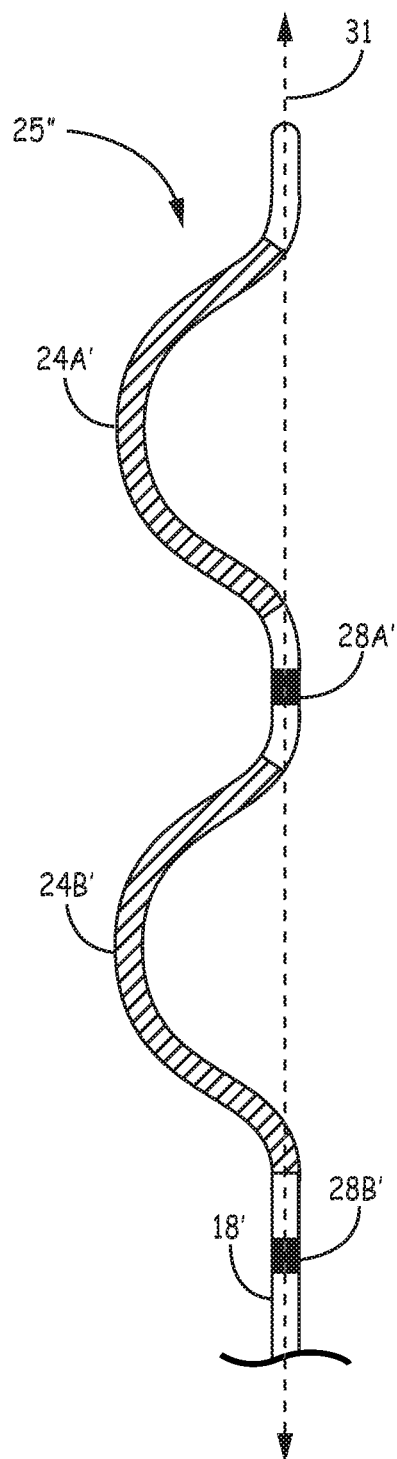
FIG. 4 is a conceptual diagram of a distal portion of an extra-cardiovascular lead having a lead body shape according to another example.

FIG. 4 is a conceptual diagram illustrating a distal portion 25" of another example of extra-cardiovascular lead 16 having an electrode arrangement similar to that of FIG. 3 but with a non-linear or curving distal portion 25" of lead body 18'. Lead body 18' may be pre-formed to have a normally curving, bending, serpentine, undulating, or zig-zagging shape along distal portion 25". In this example, defibrillation electrodes 24A' and 24B' are carried along pre-formed curving portions of the lead body 18'. Pace/sense electrode 28A' is carried between defibrillation electrodes 24A' and 24B'. Pace/sense electrode 28B' is carried proximal to the proximal defibrillation electrode 24B'.

In one example, lead body 18' may be formed having a normally curving distal portion 25" that includes two "C" shaped curves, which together may resemble the Greek letter epsilon, "ε." Defibrillation electrodes 24A' and 24B' are each carried by the two respective C-shaped portions of the lead body distal portion 25" and extend or curve in the same direction. In the example shown, pace/sense electrode 28A' is proximal to the C-shaped portion carrying electrode 24A', and pace/sense electrode 28B' is proximal to the C-shaped portion carrying electrode 24B'. Pace/sense electrodes 24A' and 24B' are approximately aligned with a central axis 31 of the normally straight or linear, proximal portion of lead body 18' such that mid-points of defibrillation electrodes 24A' and 24B' are laterally offset from electrodes 28A' and 28B'. Defibrillation electrodes 24A' and 24B' are located along respective C-shaped portions of the lead body distal portion 25" that extend laterally in the same direction away from central axis 31 and electrodes 28A' and 28B'. Other examples of extra-cardiovascular leads including one or more defibrillation electrodes and one or more pacing and sensing electrodes carried by curving serpentine, undulating or zig-zagging distal portion of the lead body that may be implemented with the pacing techniques described herein are generally disclosed in pending U.S. Pat. Publication No. 2016/0158567 (Marshall, et al.), incorporated herein by reference in its entirety.

Figure 5:
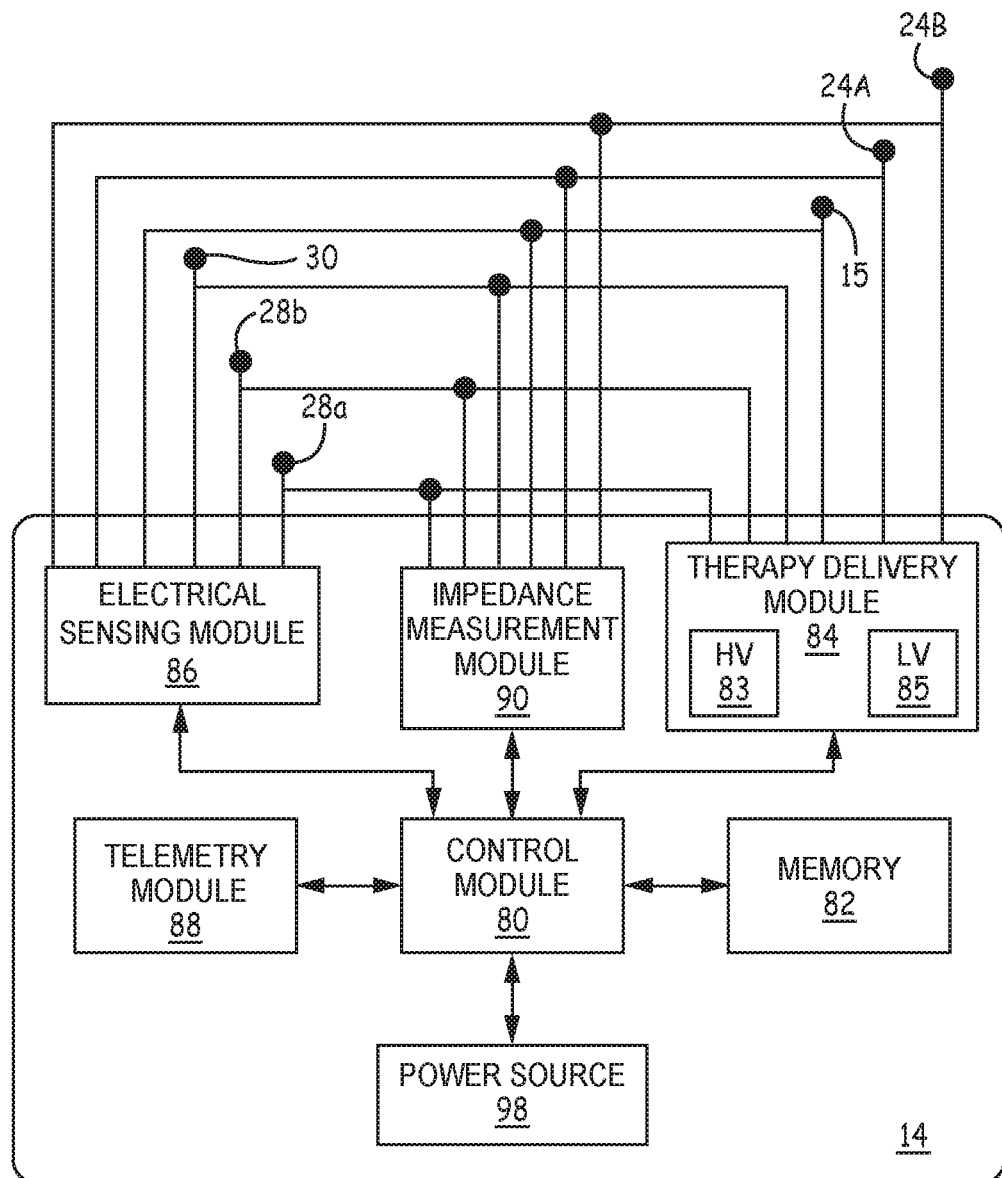
FIG. 5 is a schematic diagram of the ICD of the system of FIGS. 1A-2C according to one example.

FIG. 5 is a schematic diagram of ICD 14 according to one example. The electronic circuitry enclosed within housing 15 (shown schematically as a can electrode in FIG. 5) includes software, firmware and hardware that cooperatively monitor one or more cardiac electrical signals, determine when a pacing therapy is necessary, and deliver prescribed pacing therapies as needed. The software, firmware and hardware are also configured to determine when a CV/DF shock is necessary, and deliver prescribed CV/DF shock therapies. ICD 14 is coupled to an extra-cardiovascular lead, such as lead 16 carrying extra-cardiovascular electrodes 24A, 24B, 28A, 28B and 30, for delivering pacing therapies, CV/DF shock therapies and sensing cardiac electrical signals.

ICD 14 includes a control module 80, memory 82, therapy delivery module 84, electrical sensing module 86, and telemetry module 88. ICD 14 may include an impedance measurement module 90 for delivering a drive signal across a therapy delivery electrode vector and measuring a resulting voltage for determining an electrical impedance of the electrode vector.

A power source 98 provides power to the circuitry of ICD 14, including each of the modules 80, 82, 84, 86, 88, 90 as needed. Power source 98 may include one or more energy storage devices, such as one or more rechargeable or non-rechargeable batteries.

The connections between power source 98 and each of the other modules 80, 82, 84, 86 and 88 are to be understood from the general block diagram of FIG. 5, but are not shown for the sake of clarity. For example, power source 98 is coupled to low voltage (LV) and high voltage (HV) charging circuits included in therapy delivery module 84 for charging LV and HV capacitors, respectively, or other energy storage devices included in therapy delivery module 84 for producing electrical stimulation pulses.

The functional blocks shown in FIG. 5 represent functionality included in ICD 14 and may include any discrete and/or integrated electronic circuit components that implement analog and/or digital circuits capable of producing the functions attributed to ICD 14 herein. As used herein, the term "module" refers to an application specific integrated circuit (ASIC), an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the device and by the particular detection and therapy delivery methodologies employed by the ICD 14. Providing software, hardware, and/or firmware to accomplish the described functionality in the context of any modern ICD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14 or those ICD modules. The non-transitory computer-readable media storing the instructions may include any of the media listed above.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware, firmware or software components, or integrated within common hardware, firmware or software components. For example, cardiac pacing operations may be performed by therapy delivery module 84 under the control of control module 80 and may include operations implemented in a processor executing instructions stored in memory 82.

Control module 80 communicates with therapy delivery module 84 and electrical sensing module 86 for sensing cardiac electrical activity, detecting cardiac rhythms, and controlling delivery of cardiac electrical stimulation therapies in response to sensed cardiac signals. Therapy delivery module 84 and electrical sensing module 86 are electrically coupled to electrodes 24A, 24B, 28A, 28B, and 30 carried by lead 16 (shown in FIGS. 1A and 1B) and the housing 15, which may function as a common or ground electrode or as an active can electrode for delivering CV/DF shock pulses.

Electrical sensing module 86 may be selectively coupled to electrodes 28A, 28B, 30 and housing 15 in order to monitor electrical activity of the patient's heart. Electrical sensing module 86 may additionally be selectively coupled to electrodes 24A and/or 24B. Sensing module 86 is enabled to selectively monitor one or more sensing vectors selected from the available electrodes 24A, 24B, 28A, 28B, 30 and housing 15. For example, sensing module 86 may include switching circuitry for selecting which of electrodes 24A, 24B, 28A, 28B, 30 and housing 15 are coupled to sense amplifiers or other cardiac event detection circuitry included in sensing module 86. Switching circuitry may include a switch array, switch matrix, multiplexer, or any other type of switching device suitable to selectively couple sense amplifiers to selected electrodes. The cardiac event detection circuitry within electrical sensing module 86 may include one or more sense amplifiers, filters, rectifiers, threshold detectors, comparators, analog-to-digital converters (ADCs), or other analog or digital components.

In some examples, electrical sensing module 86 includes multiple sensing channels for acquiring cardiac electrical signals from multiple sensing vectors selected from electrodes 24A, 24B, 28A, 28B, 30 and housing 15. Each sensing channel may be configured to amplify, filter and rectify the cardiac electrical signal received from selected electrodes coupled to the respective sensing channel to improve the signal quality for sensing cardiac events, e.g., P-waves and/or R-waves. Each sensing channel includes cardiac event detection circuitry for sensing cardiac events from the received cardiac electrical signal developed across the selected sensing electrode vector(s). For example, each sensing channel in sensing module 86 may include an input or pre-filter and amplifier for receiving a cardiac electrical signal from a respective sensing vector, an analog-to-digital converter, a post-amplifier and filter, a rectifier to produce a digitized, rectified and amplified cardiac electrical signal that is passed to a cardiac event detector included in sensing module 86 and/or to control module 80. The cardiac event detector may include a sense amplifier, comparator or other circuitry for comparing the rectified cardiac electrical signal to a cardiac event sensing threshold, such as an R-wave sensing threshold, which may be an auto-adjusting threshold. Sensing module 84 may produce a sensed cardiac event signal in response to a sensing threshold crossing. The sensed cardiac events, e.g., R-waves, are used for detecting cardiac rhythms and determining a need for therapy by control module 80. In some examples, cardiac electrical signals such as sensed R-waves are used to detect capture of a pacing pulse delivered by ICD 14.

Therapy delivery module 84 includes a low voltage (LV) therapy module 85 for delivering low voltage pacing pulses using an extra-cardiovascular pacing electrode vector selected from electrodes 24A, 24B, 28A, 28B, 30 and 15. LV therapy module 85 may be configured to deliver low voltage pacing pulses, e.g., 8 V or less or 10 V or less or 15 V or less or 18 V or less. One or more capacitors included in the LV therapy module 85 are charged to a voltage according to a programmed pacing pulse amplitude by a LV charging circuit, which may include a state machine. At an appropriate time, the LV therapy module 85 couples the capacitor(s) to a pacing electrode vector to deliver a pacing pulse to the heart 26.

LV therapy module 85 is capable of operating in one or more low-voltage pacing output configurations. In one example, LV therapy module 85 may be enabled to deliver low-voltage, single pulse pacing pulses in a first low-voltage pacing output configuration.

When the capture threshold of heart 26 is higher than a maximum single-pulse pacing pulse output producible by LV therapy module 85, LV therapy module 85 may be enabled to deliver composite pacing pulses comprising two or more fused individual pulses in a second low-voltage pacing output configuration. The fused pacing pulses are delivered by sequentially discharging at least two holding capacitors or at least two holding capacitor combinations included in LV therapy module 85 to deliver at least two individual pulses that are fused in time to produce a composite pacing pulse having a greater pulse energy than a maximum pulse energy of a single pulse pacing pulse producible by LV therapy module 84. For example, the total pulse width of a fused pacing pulse is longer than the maximum single-pulse pacing pulse width that is producible by LV therapy module 84. When a single-pulse pacing pulse of a given voltage amplitude does not capture the heart, even at the maximum available pulse amplitude and width of the single pulse, a composite pacing pulse having the same voltage amplitude has a total pulse energy delivered over the composite pacing pulse width that may be greater than the capture threshold of the heart. The pulse voltage amplitude may be the maximum voltage amplitude tolerable by the patient or the maximum pulse amplitude (which may be 8 V or 10 V or 15 V or 18V in some examples) available from LV therapy module 84.

In other examples, LV therapy module 85 may only operate in one low-voltage pacing output configuration, e.g., only the single pulse low-voltage pacing output configuration, only the low-voltage fused pacing output configuration, or some other low-voltage pacing output configuration. In another example, LV therapy module 85 may be capable of operating in more than two different selectable low-voltage pacing output configurations.

High voltage (HV) therapy module 83 includes one or more high voltage capacitors. When a shockable rhythm is detected, the HV capacitor(s) is(are) charged to a voltage level by a HV charging circuit according to the programmed shock energy. The HV charging circuit may include a transformer and be a processor-controlled charging circuit that is controlled by control module 80. Control module 80 applies a signal to trigger discharge of the HV capacitor(s) upon detecting a feedback signal from therapy delivery module 84 that the HV capacitors have reached the voltage required to deliver the programmed shock energy. In this way, control module 80 controls operation of the high voltage therapy module 83 to deliver CV/DF shocks using defibrillation electrodes 24A, 24B and/or housing 15.

HV therapy module 83 may be used to deliver cardiac pacing pulses when pacing pulses delivered by LV therapy module 85 in a low-voltage pacing output configuration do not adequately capture heart 26. In this case, the HV capacitor(s) is(are) charged to a much lower voltage than that used for delivering shock therapies but may be higher than the maximum available pulse amplitude produced by the LV therapy module 85. For example, the HV capacitor may be charged to 40 V or less, 30 V or less, or 20 V or less for producing extra-cardiovascular pacing pulses. In most instances, the HV circuitry is generally designed for delivery of the high-voltage CV/DF shocks which are typically associated with voltages that are much higher than the 40 V, 30V, or 20V. For example, the voltages associated with CV/DF shocks may be at least ten times greater than those voltages. The HV circuitry of therapy delivery module 84 may only be capable of producing reduced level voltages to a certain minimum level. The minimum level may be 10V in one example. In other examples the minimum voltage level may be 15V or even 20V depending on the design.

Compared to low-voltage pacing output configurations, a longer pulse width may be utilized in the high-voltage pacing output configuration while still maintaining a pulse voltage amplitude that is greater than the pacing capture threshold when discharging the HV capacitor(s). The longer pulse width is attainable due to a higher capacitance (and consequently higher RC time constant) of the HV capacitor(s). As such, the LV therapy module 85 may be capable of producing a maximum pulse voltage amplitude of up to and including 10 V. The maximum single-pulse pacing pulse width may be 2 ms. The maximum composite pacing pulse width may be up to 8 ms or higher.

The HV therapy module 83 may be capable of producing a pulse voltage amplitude of at least the minimum voltage level attainable by the HV circuitry (e.g., 10 V or more, 15 V or more, 20 V or more). The minimum voltage level may, in some examples, be greater than the maximum voltage level of LV therapy module 85. In other examples there may be an overlap of the maximum voltage level of LV therapy module 85 (e.g., 8V in one example) and the minimum voltage level attainable by the HV therapy module 83 (e.g., 15-20 V in one example). The HV therapy module 83 may also produce mono- or multi-phasic pulses having a relatively longer pacing pulse width, e.g., 10 ms or more, because of the higher capacitance of high voltage capacitors included in HV circuitry. A typical HV pacing pulse width may be 10 ms; however an example range of available pulse widths may be 2 ms to 20 ms. An example of a maximum voltage amplitude that may be used for delivering high voltage pacing pulses may be 40 V. When a relatively higher pacing pulse voltage amplitude is tolerable by the patient, e.g., more than 10 V, a relatively shorter pacing pulse width, e.g., 2 to 5 ms, may be used during the high-voltage pacing output configuration. However, a longer pacing pulse width may be used as needed, e.g., a 10 V, 20 ms pacing pulse.

For the sake of comparison, the HV capacitor(s) of the HV therapy module 83 may be charged to an effective voltage greater than 100 V for delivering a cardioversion/defibrillation shock. For example, two or three HV capacitors may be provided in series having an effective capacitance of 148 microfarads in HV therapy module 83. These series capacitors may be charged to develop 750 to 800 V for the series combination in order to deliver shocks having a pulse energy of 5 Joules or more, and more typically 20 Joules or more. The pacing pulses delivered by the HV therapy module 83 will have a pulse energy in the milliJoule range or at least tenths of milliJoules. For instance, a pacing pulse generated by HV therapy module 83 having a 10 V amplitude and 20 ms pulse width may be in the range of 2 to 5 milliJoules when the pacing electrode vector impedance is in the range of 400 to 1000 ohms.

Composite pacing pulses, delivered by the LV therapy module 85, having an 8 V amplitude and 8 ms pulse width may be in the range of 0.5 to 1.3 milliJoules for a similar range of pacing loads as given in the preceding example. Extra-cardiovascular, single-pulse pacing pulses delivered by LV therapy module 83 that are 8V in amplitude and 2 ms in pulse width may be in the range of 0.2 to 0.3 milliJoules for pacing loads of 400 to 1000 ohms. In contrast, pacing pulses delivered using endocardial electrodes or epicardial electrodes may be on the order of microJoules, e.g., 2 microJoules to 5 microJoules for a typical endocardial pacing pulse that is 2V in amplitude, 0.5 ms in pulse width and applied across a pacing electrode vector impedance of 400 to 1000 ohms.

As will be described below, control module 80 may enable a high-voltage pacing output configuration using HV therapy module 83 by applying at least a minimum electrical current required to enable switching circuitry included in HV therapy module 83 for coupling the HV capacitor(s) to a pacing electrode vector. Circuitry included in HV therapy module 83 and LV therapy module 85 is also described in conjunction with FIGS. 9 and 11 respectively.

In some instances, control module 80 may control impedance measurement module 90 to determine the impedance of a pacing electrode vector. Impedance measurement module 90 may be electrically coupled to the available electrodes 24A, 24B, 28A, 28B, 30 and housing 15 for performing impedance measurements of one or more candidate pacing electrode vectors. Control module 80 may control impedance measurement module 90 to perform impedance measurements by passing a signal to impedance measurement module 90 to initiate an impedance measurement of a pacing electrode vector. Impedance measurement module 90 is configured to apply a drive or excitation current across a pacing electrode vector and determine the resulting voltage. The voltage signal may be used directly as the impedance measurement or impedance may be determined from the applied current and the measured voltage. The impedance measurement may be passed to control module 80.

As described in conjunction with FIG. 10 below, control module 80 may use the impedance measurement to set a variable shunt resistance included in HV therapy module 83 when a high-voltage pacing output configuration is selected for delivering extra-cardiovascular pacing pulses to heart 26. The variable shunt resistance may be parallel to the pacing load and set to be equal to or less than the pacing load impedance to maintain electrical current through HV therapy module switching circuitry throughout the duration of a pacing pulse delivered by the HV therapy module 83 thereby promoting an appropriate voltage signal across the pacing load for capturing the patient's heart.

Control parameters utilized by control module 80 for detecting cardiac rhythms and delivering electrical stimulation therapies and tachyarrhythmia induction pulses may be programmed into memory 82 via telemetry module 88. Telemetry module 88 includes a transceiver and antenna for communicating with external device 40 (shown in FIG. 1A) using RF communication as described above. Under the control of control module 80, telemetry module 88 may receive downlink telemetry from and send uplink telemetry to external device 40. In some cases, telemetry module 88 may be used to transmit and receive communication signals to/from another medical device implanted in patient 12.

Figure 6:
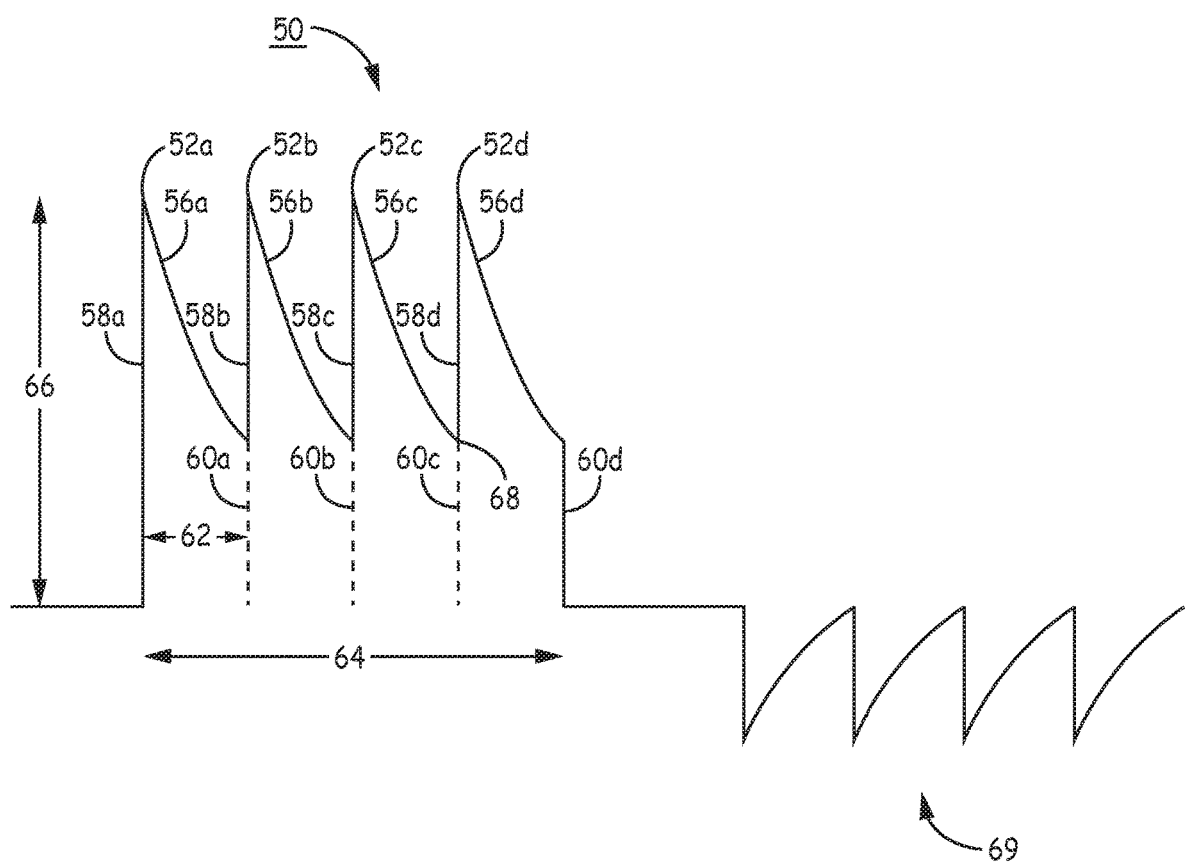
FIG. 6 is a depiction of one example of a low voltage pacing pulse that may be generated and delivered by the low voltage (LV) therapy module of the ICD of FIGS. 1A-2C to pace a patient's heart using extra-cardiovascular electrodes and a low-voltage, pacing output configuration.

FIG. 6 is a depiction of one example of a composite pacing pulse 50 that may be generated and delivered by LV therapy module 85 of ICD 14 to pace heart 26 using extra-cardiovascular electrodes when a low-voltage, fused pacing output configuration is selected by control module 80. Pacing pulse 50 is a composite pacing pulse comprising four pulses 52a, 52b, 52c, and 52d that are each individually delivered by discharging a LV holding capacitor (or a combination of parallel LV holding capacitors) across a selected pacing electrode vector via a respective output capacitor included in a capacitor array of LV therapy module 85. Discharging a single LV holding capacitor (or combination of parallel LV holding capacitors simultaneously) results in delivery of a single, low-voltage pacing pulse by LV therapy module 85. In one low-voltage pacing output configuration, LV therapy module 85 is enabled to discharge multiple LV holding capacitors in a sequential manner across a selected pacing electrode vector such that multiple single low-voltage pacing pulses are delivered sequentially to produce a composite pacing pulse 50 that elicits a single evoked response by the myocardium.

The first pulse 52a defines a leading edge 58a of the composite pulse 50. Each of the pulses 52a-52d has a peak voltage amplitude 66 according to a programmed pulse amplitude. A decaying portion 56a, 56b, 56c, and 56d of each respective pulse decays according to an RC time constant of the discharge circuit of LV therapy module 85. Each individual pulse 52a-52d may be truncated at an individual pulse width 62. The leading edge 58b, 58c and 58d of the respective pulses 52b, 52c and 52d coincides in time with the terminating edge 60a, 60b and 60c, respectively of the immediately preceding pulse, 52a, 52b, and 52c, respectively. The terminating edge 60d of the final pulse 52d defines the trailing edge of the composite pulse 50.

The composite pulse 50 has a time-varying pulse amplitude that reaches the maximum pulse amplitude 66 at the leading edge 58a-58d of each pulse with periods of decay between the leading edges 58a-58d to the minimum pulse amplitude 68 just prior to the next leading edge. The individual pulse width 62 may be set to maintain the minimum pulse amplitude 68 of each individual pulse 52a-52d just prior to the next individual pulse above a minimum amplitude threshold to ensure that the total pulse energy delivered in the composite pulse 50 successfully captures and paces the heart 26. The individual pulse width 62 may be fixed, e.g., up to 2 ms in some examples so that the total pulse width is up to 8 ms when four fused, consecutive pulses 52a-52b are delivered as shown in the example of FIG. 6. The individual pulse width 62 may be a maximum pulse width available from LV therapy module 85 when a single holding capacitor is discharged across the pacing electrode vector. This maximum single pulse width may be limited by the decay rate of the pacing pulse as determined by the RC time constant of the discharge circuit. For a given pacing pulse width, a pacing capture threshold amplitude can be identified as the lowest pacing pulse amplitude that elicits an evoked response (depolarization) of the myocardial tissue. The decay rate of a single pacing pulse determined by the RC time constant may cause the amplitude of the pacing pulse to fall below a myocardial pacing capture threshold amplitude before the single pacing pulse width that is required to achieve myocardial capture for the given pacing pulse amplitude can be reached. If the pacing pulse amplitude is set to a maximum available value, e.g., 8 Volts or 10 Volts, the maximum pacing pulse width of a single pacing pulse as determined by the RC time constant may be insufficient to deliver the pulse energy required to capture the heart using a selected extra-cardiovascular pacing electrode vector. As such, a composite pacing pulse, having a total pulse width that is greater than the maximum available pulse width of a single pacing pulse, may be required to achieve a total pulse energy sufficient to capture the heart.

The individually delivered pulses are fused in time such that the individual pulse energy is cumulative in producing a total pulse energy that is greater than the pacing capture threshold of the patient's heart, even though each individual pulse 52a-52d may have a pulse energy that is less than the pacing capture threshold. The number of individual pulses delivered (which may be more or less than four in some examples) in fused sequence may be selected based on the total pacing pulse width 64 required to capture the heart for a given pulse amplitude 66, and the maximum individual pulse width 62 that can be reached without allowing the minimum pulse amplitude 68 to fall below a minimum amplitude threshold for a time period between the fused pulses that prevents the pulses from having a cumulative dose effect for capturing the myocardium. For example, the minimum pulse amplitude 68 may be prevented from reaching 0 V between individual pulses and may be maintained above an amplitude threshold, which may be defined as a percentage of the programmed pulse amplitude 66, e.g., 25%, 50% or other selected percentage of programmed pulse amplitude 66.

The terminating edges 60a, 60b, and 60c of respective pulses 52a-52c occur nearly simultaneously with leading edges 58b, 58c, and 58d of the respective subsequent pulses 52b, 52c, and 52d within the limits of the electronic circuitry. It is recognized that limitations within the electronic circuitry may result in a non-zero time gap between individual pulses 52a-52d in some examples. The delivered energy of each individual pulse 52a-52d, however, is fused close enough in time to a preceding and/or subsequent individual pulse such that the individual pulse energies accumulate to achieve a dose response necessary to achieve capture of the patient's heart. Each individual pulse 52a-52d may have a pulse energy below the capture threshold of the heart. By delivering the individual pulses 52a-52d within a time window defined by the total pulse width 64, the total composite pacing pulse energy that is delivered is greater than the pacing capture threshold of the heart. As such, the composite pulse captures the heart even when each individual pulse 52a-52d delivered alone or spaced further apart in time may be insufficient to capture and pace the heart.

Each individual pulse 52a-52d may be delivered across the pacing electrode vector having the same polarity (positive-going in the example shown) by sequentially coupling different capacitance elements (a single capacitor or a combination of two or more capacitors) across the selected pacing electrode vector. Each of the different capacitance elements are charged to the peak voltage amplitude 66 prior to being coupled across the pacing electrode vector. In some examples, the same capacitor or combination of capacitors may not be used to deliver two consecutive individual pulses, e.g., pulses 52a and 52b, since charging of the capacitor (or combination of capacitors) to the peak voltage amplitude 66 occurs prior to initiating each respective one of the individual pulses 52a-52d. The same capacitor or same combination of capacitors may be used to deliver two non-consecutive individual pulses, e.g., 52a and 52d, by recharging the same capacitor or combination of capacitors to the peak voltage amplitude 66 during the intervening one or more individual pulses 52b and 52c.

Each individual pulses 52a-52d is shown to have the same peak voltage amplitude 66 in FIG. 6. The peak voltage amplitude may be the maximum voltage amplitude available from the LV therapy module 85 or a maximum voltage amplitude tolerable by the patient. The total pulse energy of the composite pacing pulse 50 may be controlled by setting the individual pulse number and individual pulse width of pulses 52a-52d. It is contemplated, however, that one capacitor (or combination of capacitors) that is discharged to deliver one of the individual pulses 52a-52d may be charged to a different voltage than another capacitor (or combination of capacitors) used to deliver a different one of the individual pulses 52a-52d. As a result, the individual pulses 52a-52d may have different peak voltage amplitudes (and/or polarity) in some instances. Individual pulses 52a-52d, however, are generated by switching out a first discharging capacitor (or combination of capacitors) and switching in a next capacitor (or combination of capacitors) that is(are) charged to the desired peak voltage amplitude of the next individual pulse. A first individual pulse is thereby terminated by stopping discharging of the first capacitor(s), and the next individual pulse is started by starting discharging of the next capacitor(s).

In some examples, the pacing pulse amplitude may be monitored in real time during the delivery of composite pacing pulse 50, and, when the decaying amplitude drops to an amplitude threshold value, the next individual pulse is started. For example, the amplitude of decaying portion 56a may be sampled, and when the minimum amplitude 68 is reached the next pulse 52b is started. The first pulse 52a is truncated when the next pulse 52b is started so that terminating edge 60a of pulse 52a and leading edge 58b of the second pulse 52b occur simultaneously. Pacing pulse 50 is followed by a recharge pulse 69 comprising a low amplitude pulse in opposite polarity for each of the individual pulses 52a-52d. The recharge pulse 69 may allow an output capacitor of the LV therapy module 85 to passively discharge if it has charged during the delivery of pacing pulse 50 to promote charge neutrality and may reduce polarization artifact of the pacing electrodes.

In other examples, the individual pulses 52a through 52d of composite pacing pulse 50 may be overlapping in that the leading edge 58b, 58c or 58d of pulses 52b, 52c and 52d, respectively, may slightly precede the respective terminating edge 60a, 60b or 60c of the respective preceding pulses 52a, 52b and 52c. While individual pulses 52a-52d are shown each having an equal individual pulse width 62, it is contemplated that individual pulses 52a-52d may have differing individual pulse widths, which may be based on the effective capacitance of a holding capacitor or holding capacitor combination that is being discharged to produce the individual pulses 52a-52d. For example, a composite pacing pulse of 8.0 ms may be produced by delivering two individual pulses each having a pulse width of 2.0 ms by discharging two different holding capacitors in a sequential manner followed by a third individual pulse having a pulse width of 4.0 ms produced by discharging two parallel holding capacitors simultaneously. A composite pulse of this type and other techniques for producing a composite pacing pulse including multiple individual pulses delivered in fused succession are generally disclosed in provisional U.S. Pat. Application No. 62/262,412 and the corresponding U.S. Pat. Application Publication No. 2017/0157399 filed on the same day herewith), the content of which is incorporated herein by reference in its entirety.

The composite pacing pulse 50 is produced to provide a pacing pulse having a total pulse energy within the total composite pacing pulse width 64 that is adequate to capture the heart by producing an evoked depolarization response of the heart. As described below, a low-voltage, fused pacing output configuration may be selected by control module 80 when a low-voltage single pulse pacing output configuration does not satisfy pacing capture threshold criteria. Alternatively, the LV composite pacing pulse output configuration may be the only LV pacing output configuration.

Figure 7:
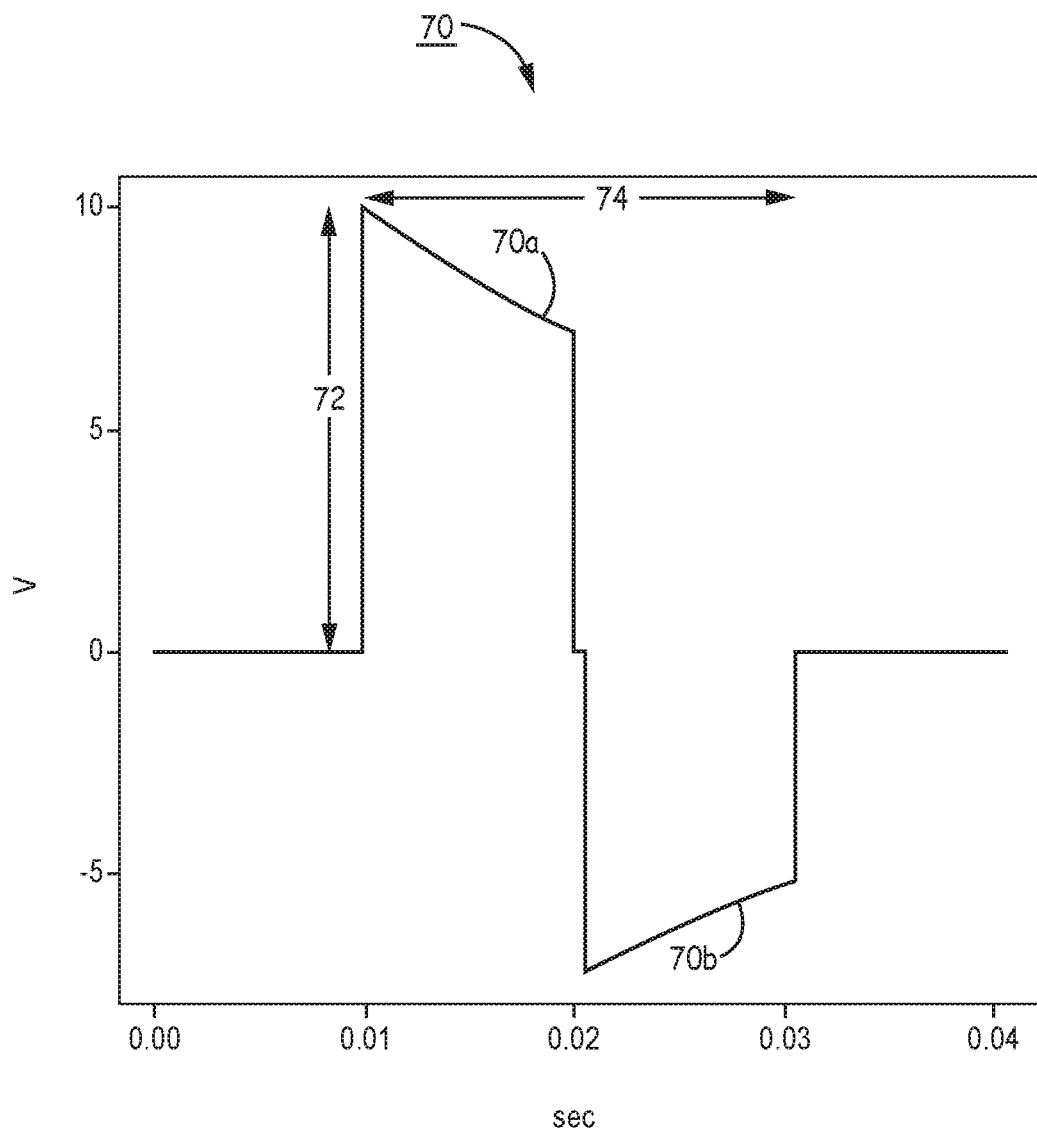
FIG. 7 is a depiction of one example of a high voltage pacing pulse that may be generated and delivered by the high voltage (HV) therapy module of the ICD of FIGS. 1A-2C to pace a patient's heart using extra-cardiovascular electrodes and a high-voltage, pacing output configuration.

FIG. 7 is a depiction of one example of a high voltage pacing pulse 70 that may be generated and delivered by HV therapy module 83 of ICD 14 to pace heart 26 using extra-cardiovascular electrodes when a high-voltage pacing output configuration is selected by control module 80. When low voltage pacing pulses delivered by LV therapy module 85 are determined to inadequately capture heart 26, by either a low-voltage, single-pulse pacing output configuration or a low-voltage, fused pacing output configuration, control module 80 is configured to automatically enable HV therapy module 83 to deliver cardiac pacing pulses. HV therapy module 83 may produce a high voltage pacing pulse 70 having a programmed pacing pulse amplitude 72 that is greater than the maximum voltage amplitude that LV therapy module 85 can produce but is much less than the voltage amplitude of CV/DF shock pulses required to cardiovert or defibrillate the heart 26. For example, high voltage pacing pulse amplitude 72 may be greater than or equal to 10 V and up to 40 V, inclusive, or may be from 10 V to 30 V in other examples. In another example, high voltage pacing pulse amplitude is greater than 8 V, up to and including 40 V. The high voltage pacing pulse 70 may have a pulse energy that is less than a defibrillation threshold of the heart 26. In the example shown, pacing pulse 70 has a pulse voltage amplitude of 10 V and a pulse width 74 of 20 ms. In another example, pacing pulse 70 has a pulse voltage amplitude equal to or between 10 and 20 V and a pulse width of 10 ms.

The pulse width 74 may depend on the pacing pulse amplitude 72 such that the total pacing pulse energy delivered by pulse 70 having amplitude 72 and width 74 successfully captures and paces heart 26, but may be less than a defibrillation threshold. In some examples, the pulse width 74 may be from 1 ms up to and including 10 ms, but may be shorter than or longer than this example range. The pulse width 74 may be set according to a pulse width threshold determined for the programmed pacing pulse amplitude 72. For example, if the pulse amplitude is set to 20 V, the minimum pulse width that successfully captures the heart may be determined during a pacing capture threshold test. Pacing pulse width 74 may be set at a safety pacing margin longer than the capture threshold pulse width. Alternatively, pulse width 74 may be set first and pulse amplitude 72 may be set to an amplitude that is a safety margin above the capture threshold pulse amplitude found during a pacing capture threshold test using the selected pulse width 74 when HV therapy module 83 is enabled to deliver pacing pulses in a high-voltage pacing output configuration.

As shown, pacing pulse 70 is a biphasic pacing pulse having a first, positive-going portion 70a and a second, negative going portion 70b. A biphasic pacing pulse 70 may be produced by HV therapy module 83 through the control of switching circuitry included in HV therapy module 83. Switching circuitry of HV therapy module 83 may controlled to reverse the polarity of the delivered pulse during capacitor discharging to produce the biphasic pulse. The polarity may be reversed at a given voltage threshold in some examples. The HV capacitor charged to the pulse voltage amplitude 72 continues to be discharged for the remaining portion 70b of pacing pulse width 74. As can be observed in FIG. 7, the ending voltage amplitude of the positive-going portion 70a is the starting voltage amplitude of the negative-going portion 70b because the same capacitor(s) continue to be discharged after switching circuitry reverses the polarity of the pacing pulse 70. In contrast, the individual pulses 52a-52d of the composite pacing pulse 50 of FIG. 6 are each produced by switching to a different capacitor (or combination of capacitors) that has been charged to the pulse voltage amplitude 66 to begin the next individual pulse. Each individual pulse 52a-52d is produced by discharging a different capacitor (or combination of capacitors) across the pacing electrode vector resulting in individual pulses each having a leading pulse amplitude equal to the pulse amplitude 66. In other examples, high voltage pacing pulse 70 may be delivered as a monophasic, other multi-phasic, or other shaped pulse through the control of the switching circuitry.

Figure 8:
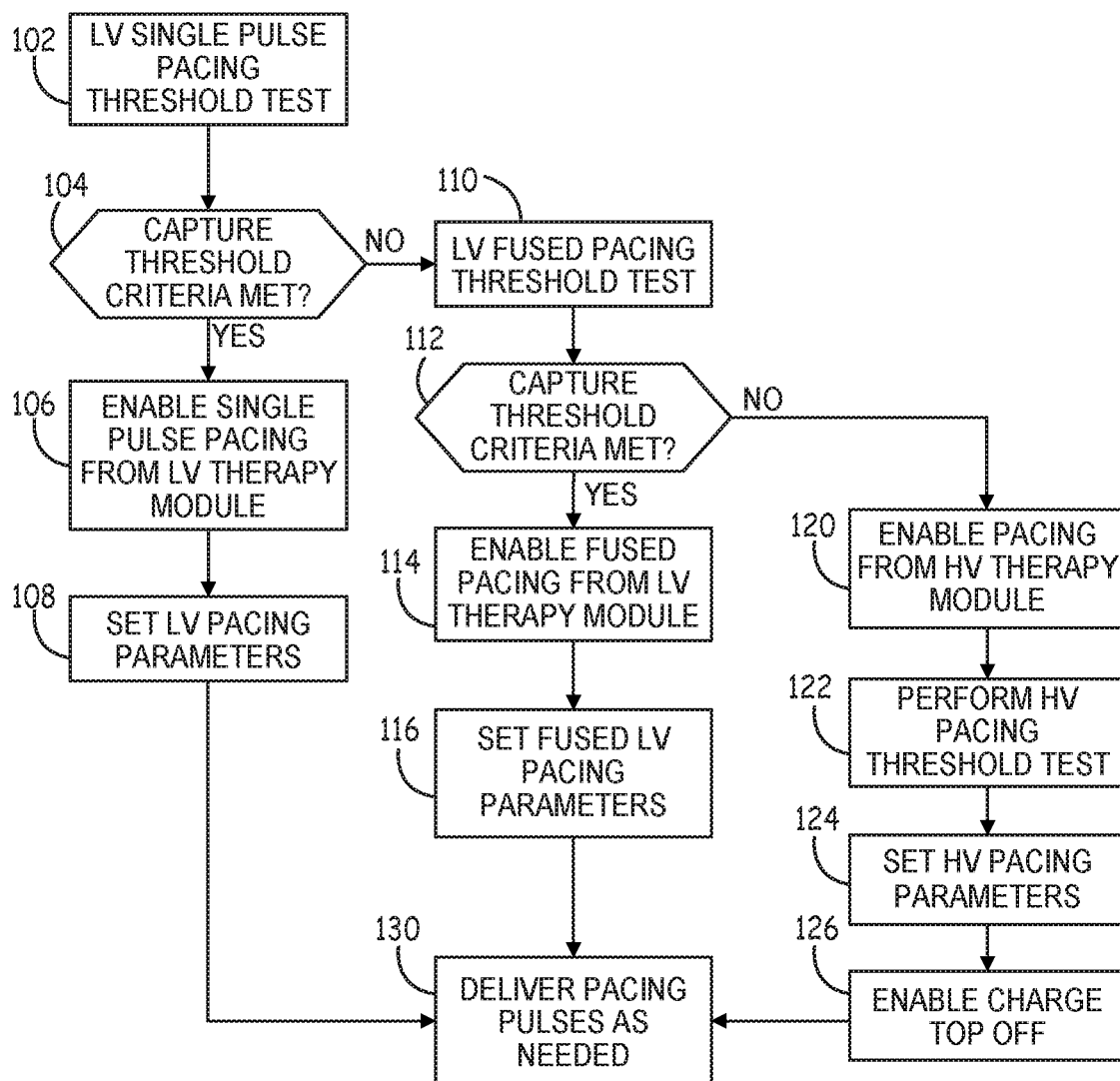
FIG. 8 is a flow chart of one method for selecting a pacing output configuration for use in delivering extra-cardiovascular cardiac pacing pulses by the ICD of FIGS. 1A-2C.

FIG. 8 is a flow chart 100 of one method for selecting a pacing output configuration for use in delivering extra-cardiovascular cardiac pacing pulses by ICD 14.

In some patients, capture of heart 26 may be achievable using single, non-fused low voltage pacing pulses. In this case, control module 80 may configure the pacing output configuration to be a low-voltage, single pulse pacing output configuration using LV therapy module 85. In other patients, the pacing capture threshold may be greater than the maximum output of a single pulse produced by LV therapy module 85. In other words, the pacing capture threshold is greater than the maximum available pulse amplitude and/or greater than the maximum available single pulse width produced by LV therapy module 85, e.g., when a single holding capacitor is discharged across a pacing electrode vector. In that case, control module 80 enables a higher-energy pacing pulse output configuration than the low-voltage, single pulse pacing output configuration.

The higher energy pacing pulse output configurations available may include a low-voltage, fused pacing pulse output configuration in which composite pacing pulses, such as composite pacing pulse 50 shown in FIG. 6, are delivered by LV therapy module 85. Another higher energy pacing pulse output configuration may be a high-voltage pacing output configuration in which high voltage pacing pulses, e.g., pulse 70 shown in FIG. 7, are delivered by HV therapy module 83.

As used herein, a "high voltage pacing pulse" is a pacing pulse produced by the HV therapy module 83 by discharging a HV capacitor that is charged to a voltage that is greater than a maximum voltage that a LV capacitor including in LV therapy module 85 can be charged to. As described below, the HV therapy module 83 includes a HV charging circuit having a transformer used to increase the voltage available for charging the HV capacitor under the control of a processor. In comparison, the LV therapy module 85 includes a LV charging circuit that may be controlled by a state machine and uses a multiple of the battery voltage of power source 98, e.g., four times the battery voltage.

In order to determine the most appropriate pacing output configuration, pacing capture threshold tests using one or more of the available pacing output configurations may be performed. The pacing capture threshold test may be performed upon ICD implantation, on a scheduled periodic basis, upon detecting or predicting a heart rhythm requiring therapy, detecting loss of capture, or detecting a lead issue or other condition that may be indicative of a loss of capture. Control module 80 determines an appropriate pacing output configuration that is capable of reliably capturing and pacing the heart while minimizing the energy required to produce pacing pulses and minimizing patient discomfort caused by the extra-cardiovascular pacing pulses. Control module 80 selects the pacing output configuration from among at least one low-voltage pacing output configuration that uses LV therapy module 85 and one high-voltage pacing output configuration that uses HV therapy module 83.

The low-voltage pacing output configuration(s) and the high voltage pacing output configuration may deliver pacing pulses using a pacing electrode vector selected from any of the extra-cardiovascular electrodes carried by an extra-cardiovascular lead coupled to ICD 14, e.g., lead 16 shown and described in conjunction with FIGS. 1A-4. In one example, the low-voltage pacing output configuration delivers pacing pulses via one or more of electrodes 28A or 28B, or the housing 15, e.g., between one of electrodes 28A and 28B as a cathode (or anode) and the housing electrode as an anode (or cathode) or between electrode 28A as a cathode (or anode) and electrode 28B as an anode (or cathode). The high-voltage pacing output configuration may deliver pacing pulses via the defibrillation electrodes 24A and 24B, one serving as the anode (or cathode) and the other as the cathode (or anode), or between one of the defibrillation electrodes 24A or 24B paired with the housing 15. The low-voltage and high-voltage pacing output configurations are not limited for use with a particular pacing electrode vector. The pacing electrode vectors used for the low-voltage pacing output configuration and the high-voltage pacing output configuration may be selected based on individual patient need and the particular lead and electrode configuration being used and its placement in the patient's body.

Beginning at block 102, control module 80 may start a low-voltage, single pulse pacing capture threshold test. LV therapy module 85 may be controlled to deliver low-voltage, single-pulse pacing pulses according to a capture threshold test algorithm in order to determine if successful capture can be achieved using a pulse amplitude and pulse width that are within acceptable capture threshold limits for using the low-voltage, single pulse pacing output configuration. The LV single-pulse pacing capture threshold test performed at block 102 may be performed automatically by ICD 14 when control module 80 is configured to control LV therapy module 85 to deliver pacing pulses according to a capture threshold search algorithm including automatic capture detection by control module 80. In other examples, the LV, single-pulse pacing threshold test, and other capture threshold tests described herein, may be performed in a semi-automatic way in response to user-entered programming commands received from external device 40.

In some examples, the pacing capture threshold test begins at block 102 with a relatively low pacing pulse amplitude, e.g., 1 V, and a maximum available pulse width, e.g., 1.5 ms or 2.0 ms. Capture may be detected by control module 80 automatically, for example based on detecting an evoked R-wave from a cardiac electrical signal received by sensing module 86 within an expected time interval after delivering a pacing pulse.

Alternatively, capture may be verified manually by a user observing an ECG signal provided by sensing module 86 and transmitted to external device 40 by telemetry module 88. The user may enter a command into external device 40 transmitted back to ICD 14 indicating that capture is confirmed.

If capture is not detected or verified at the starting pulse amplitude and maximum pulse width, the pulse amplitude may be increased in 1 V increments or other voltage steps until capture is achieved or until a maximum test pulse amplitude is reached. In some examples, the maximum test pulse amplitude is the maximum pulse amplitude available from the LV therapy module 85. In other examples, the maximum test pulse amplitude is the maximum amplitude available from the LV therapy module 85 minus a predetermined safety margin. If capture cannot be achieved at a pulse amplitude that is at least a safety margin below the maximum available pulse amplitude, the capture threshold may be considered unacceptable for extra-cardiovascular pacing using the low-voltage, single pulse pacing output configuration.

In one example, the programmed safety margin is set equal to the pacing capture threshold for extra-cardiovascular pacing. In other words, the final pacing pulse amplitude is set to double the capture threshold voltage amplitude. For instance, if the capture threshold is 3 V, the safety margin is also 3 V so that the pacing pulse amplitude is set to 6 V. If the pacing capture threshold amplitude is determined to be 5 V, the required safety margin is 5 V resulting in 10 V for the pacing pulse amplitude, which may exceed the maximum available pulse amplitude of LV therapy module 85. In other examples, the safety margin may be a fixed increment greater than the pulse amplitude capture threshold, for example 2 V greater than the pacing amplitude capture threshold. If the pacing capture threshold plus the safety margin is equal to or exceeds the maximum available pulse amplitude available for the LV therapy module 85, the pacing capture threshold may be determined to be unacceptable for low-voltage, single pulse pacing at block 104. The control module 80 advances to block 110 to perform a pacing threshold test for low-voltage fused pacing pulses.

In other examples, control module 80 may begin the LV pacing threshold test performed at block 102 by controlling LV therapy module 85 to deliver a test pacing pulse at a maximum output available for a low-voltage, single pulse. For example, the maximum output may be a pulse that is 8V in amplitude and 1.5 ms or 2.0 ms in pulse width. Control module 80 determines if this maximum-output pacing pulse captures the heart 26 based on detection of an R-wave following a pacing pulse from the cardiac electrical signal received by sensing module 86 or receipt of manual confirmation by a user. If a single-pulse pacing pulse delivered at the maximum output of LV therapy module 85, i.e., maximum available pulse amplitude and maximum available pulse width, does not capture, the pacing capture threshold is greater than the available pulse energy of a low-voltage, single-pulse, pacing output configuration. The capture threshold is not acceptable for implementing this output configuration as determined at block 104. Control module 80 advances to block 110 to perform a pacing threshold test using a low-voltage, fused pacing output configuration.

If the maximum pulse output does capture the heart during the LV pacing threshold test performed at block 102, the pacing pulse output may be decreased by decreasing the pulse amplitude and/or the pulse width in an incremental manner until loss of capture is detected by control module 80 based on cardiac electrical signals received by sensing module 86 (or manual confirmation). In other examples, the pacing threshold test performed at block 104 may include increasing pulse width from a starting pulse width and/or decreasing pulse width from a starting pulse width. For example, pulse amplitude may be increased from a starting pulse amplitude that is at least a safety margin below the maximum available pulse amplitude, and pacing pulses may be delivered at a given test voltage amplitude for one or more pulse widths. If the pacing pulse amplitude reaches a maximum test amplitude and capture has not been detected, the pulse width may be increased from a starting pulse width up to a maximum test pulse width. The pacing capture threshold may be determined as the minimum pulse amplitude for a given pulse width or the minimum pulse width for a given pulse amplitude that results in capture.

Control module 80 compares the pacing capture threshold to acceptable threshold criteria at block 104. Acceptable threshold criteria applied to the threshold test results may include a maximum acceptable pulse amplitude and/or a maximum acceptable pulse width. For example, if the capture threshold is not at least an amplitude safety margin below the maximum available pulse amplitude and/or a time interval safety margin below a maximum available pulse width, the capture threshold is unacceptable for the low-voltage, single-pulse pacing output configuration. In one example, acceptable capture threshold criteria includes a pulse amplitude capture threshold that is less than half the maximum pacing pulse amplitude available from the LV therapy module 85 when the pulse width is the maximum pulse width available from the LV therapy module 85. To illustrate, if the maximum output capability of LV therapy module 85 is an 8 V, 2.0 ms pacing pulse, the acceptable capture threshold criteria requires successful capture at a pulse amplitude that is 4 V or less when the pulse width is 2.0 ms.

If the pacing capture threshold determined at block 102 satisfies the acceptable capture threshold criteria applied at block 104, control module 80 enables the low-voltage, single-pulse pacing from the LV therapy module at block 106. LV pacing parameters are set at block 108 for controlling extra-cardiovascular pacing delivered by LV therapy module 85. The LV pacing parameters set at block 104 may be based on the capture threshold results. For example, the pacing pulse amplitude may be set to a safety margin greater than the pulse amplitude capture threshold, and the pacing pulse width may be set to the test pulse width used to determine the pulse amplitude capture threshold or to a maximum available pulse width. In one example, the LV pacing parameters set at block 108 include setting the pulse amplitude to twice the capture threshold amplitude and setting the pulse width to the maximum available pulse width.

It is recognized that in some examples, if the capture threshold criteria are unmet at block 104, a low-voltage, single pulse pacing threshold test may be repeated using a different pacing electrode vector and/or after repositioning the extra-cardiovascular lead 16. Successful capture using the low-voltage, single pulse pacing output configuration may be achieved when a different pacing electrode vector and/or different lead position may enable.

If capture threshold criteria for the low-voltage, single pulse pacing output configuration cannot be satisfied at block 104, the control module 80 starts a low-voltage, fused pacing threshold test at block 110. The low-voltage fused pacing threshold test may be started by controlling LV therapy module 85 to deliver a test composite pacing pulse at a starting test pulse amplitude and starting composite pulse width. The starting composite pulse width is defined by the number of individual pulses delivered and their respective individual pulse widths. For example, the starting test pulse amplitude may be at the maximum available pulse amplitude (e.g., 8 V) or a lower pulse amplitude that is at least a safety margin less than the maximum available pulse amplitude of LV therapy module 85.

The starting test composite pulse width may be the maximum composite pulse width available, e.g., 8 ms if up to four consecutive fused pulses each having a 2.0 ms individual pulse width are delivered. In other examples, the maximum composite pulse width may be 10 ms, 12 ms or more. Alternatively, the starting composite pulse width may be less than the maximum composite pulse width available, e.g., at least two individual, fused pulses of 2 ms each for a 4 ms composite pulse width. In some examples, the starting test pulse is delivered at a maximum amplitude and/or composite pulse width output setting available that still satisfies the capture threshold criteria. For example, the starting pulse amplitude may be an amplitude safety margin less than the maximum available pulse amplitude, and/or the starting composite pulse width may be a pulse number (or time interval) safety margin less than the maximum number of individual sequential pulses (or maximum composite pulse width) producible by the LV therapy module 85.

Safety margins may be defined for the pulse amplitude and/or for the pulse width for the low-voltage, single-pulse pacing output configuration. Similarly, safety margins may be defined for the pulse amplitude and/or composite pulse width (or total number of individual pulses) for the low-voltage fused pacing output configuration. These pulse amplitude safety margins and pulse width safety margins may be defined the same or uniquely for the low-voltage, single-pulse pacing output configuration and for the low-voltage fused pacing output configuration. The pulse amplitude safety margins may be defined as a fixed voltage or as a percentage of the pulse amplitude capture threshold. The pulse width safety margins may be defined in milliseconds or as a percentage of the pulse width capture threshold or as a pulse number (of individual pulses each having an individual pulse width) in the case of the low-voltage, fused pacing output configuration.

Capture of heart 26 by a test composite pacing pulse is detected automatically by control module 80, e.g., based on an R-wave sensed from the cardiac electrical signal received by sensing module 86 following the pacing pulse and/or based on other analysis of the cardiac electrical signal received by sensing module 86. Alternatively, capture is verified by a user interacting with external device 40. If capture is verified after delivery of a composite pacing pulse that meets the acceptable capture threshold criteria, applied at block 112, control module 80 enables the low-voltage, fused pacing output configuration at block 114. Acceptable capture threshold criteria may include a maximum pulse amplitude capture threshold and/or maximum composite pulse width capture threshold. For example one or both of the pulse amplitude capture threshold or the composite pulse width threshold may be required to be at least a respective safety margin less than the maximum available pulse amplitude and/or less than the maximum available composite pulse width. To illustrate, the acceptable capture threshold criteria applied at block 112 may require the pulse amplitude capture threshold be equal to or less than 50% of the maximum available pulse amplitude when the maximum composite pulse width is delivered. For instance if the maximum output for the low-voltage, fused pacing output configuration is a composite pulse having an amplitude of 8 V and composite pulse width of 8 ms, the acceptable capture threshold criteria applied at block 112 may be a maximum pulse amplitude threshold of 4 V when the total composite pulse width is 8 ms.

If the acceptable capture threshold criteria are met, control module 80 enables the low-voltage, fused pacing output configuration at block 114. As described below, the low-voltage, fused pacing output configuration may be enabled by control module 80 by enabling or activating switches included in LV therapy module 85 that allow multiple LV holding capacitors to be sequentially discharged to a single output line across a selected pacing electrode vector.

The selected pacing electrode vector for delivering low-voltage, fused pacing pulses may be the same as the pacing electrode vector that would be used if the low-voltage, single pulse pacing output configuration had been enabled. In other words, the two different low-voltage pacing output configurations may be controlled to use the same or different pacing electrode vectors. The two low-voltage pacing output configurations (and the high-voltage pacing output configuration) are not defined by or limited to any particular pacing electrode vector. As used herein, the "pacing output configuration" refers to how the pacing pulses are produced by the LV therapy module 85 or the HV therapy module 83. The pacing output configuration is not defined by or limited to a particular pacing electrode vector used to deliver pacing pulses produced by the selected pacing output configuration.

The low-voltage fused pacing control parameters are set by control module 80 at block 116. These control parameters may include the pacing pulse amplitude and the composite pacing pulse width. The pacing pulse amplitude may be set a respective safety margin above the pulse amplitude capture threshold or to a maximum available pulse amplitude, e.g., 8 V. The composite pacing pulse width may be set to a respective safety margin longer than the pulse width capture threshold or to a maximum available composite pulse width or pulse number, e.g., 8 ms or four individual pulses. The composite pacing pulse width may be set to at least twice the maximum pulse width available for the single pacing pulse with the composite pacing pulse including at least two fused individual pulses.

If the fused pacing threshold test performed at block 110 does not result in the capture threshold criteria being satisfied at block 112, control module 80 may repeat the fused pacing threshold test using a different pacing electrode vector and/or after repositioning the extra-cardiovascular lead 16. Successful capture using the low-voltage, fused pacing output configuration may be achieved when a different pacing electrode vector and/or different lead position is available. If the fused pacing threshold test still does not result in the capture threshold criteria being satisfied at block 112, control module 80 enables a high-voltage pacing output configuration at block 120. As described below, enabling the high-voltage pacing output configuration by control module 80 may include setting a variable shunt resistance for delivering at least a minimum electrical current to switches included in HV therapy module 83 to maintain desired switches in an active or closed state during a pacing pulse.

A capture threshold test may be performed at block 122 to determine appropriate high-voltage pacing control parameters that are set at block 124. The capture threshold test may be performed by controlling HV therapy module 83 to deliver one or more pacing pulses and determining whether capture occurred, automatically by control module 80 or manually by a user as described previously herein.

The HV therapy module 83 may be configured to deliver pacing pulses in the range of 10 V to 40 V, inclusive, in one example. The capture threshold test may be initiated by delivering a test pacing pulse having a pulse amplitude at or near the minimum pacing pulse amplitude available from HV therapy module 83, e.g., 10 V. The test pulse may also be delivered at a relatively narrow or minimum available pacing pulse width. In one example, the starting test pulse delivered during the capture threshold test at block 122 is a 10 V pulse having a 2 ms pulse width. If capture is achieved, the pacing control parameters for the high-voltage pacing output configuration are set at block 124.

In an illustrative example, the pacing control parameters set at block 124 may include a pulse amplitude of 10 V and a pulse width of 10 ms when the 10 V, 2 ms pulse successfully captures heart 26. The leading edge voltage amplitude of the pacing pulse may cause pain or discomfort to the patient due to extra-cardiac capture of excitable tissue such as skeletal muscle. As such, the HV pacing control parameters may include a pacing pulse amplitude set to the minimum pulse amplitude that captures the patient's heart at a relatively short test pulse width, e.g., 2 ms, and a pacing pulse width that is set at to a relatively large safety margin greater than the test pulse width. The safety margin may be a fixed interval, e.g., 6 ms, 8 ms, 10 ms or other predetermined interval, greater than the test pulse width. Alternatively, the safety margin may be defined as a multiple of the test pulse width such as two times, three times, four times, five times, or other predetermined multiple. A maximum pulse width limit may be defined in some examples. In one example, the capture threshold test is performed at a pulse width of 2 ms, and a safety margin of 8 ms is added to the 2 ms test pulse width to set the high-voltage pacing pulse width at 10 ms. The leading edge voltage of the HV pacing pulses is not increased above the capture threshold amplitude during pacing, but the large pulse width safety margin used in this case provides a high likelihood of successfully capturing the heart.

If the starting test pulse does not capture the heart, control module 80 may control the HV therapy module 83 to deliver test pacing pulses at higher voltage amplitudes and/or pulse widths. In one example, the threshold test for the high-voltage, pacing output configuration includes delivering pacing pulses having a pulse width of 2 ms at a starting pulse amplitude of 10 V and increasing the voltage until a pulse amplitude capture threshold is identified up to a maximum of 40 V for the 2 ms pacing pulses.

The pacing control parameters set at block 124 include setting the pacing pulse amplitude to the pacing capture threshold voltage amplitude and a pacing pulse width of 10 ms. In some cases, an amplitude safety margin may be added to the pulse amplitude capture threshold to set the pacing pulse amplitude at block 124 in addition to setting the pacing pulse width to 10 ms, which may be a maximum available pacing pulse width for the high-voltage pacing output configuration. In other examples, longer pacing pulse widths may be available, but, for a given pacing pulse amplitude, the delivered energy of a pacing pulse that is longer than 10 ms may not increase significantly due to the decay rate of the pacing pulse.

At block 126, control module 80 may enable top-off charging of a high voltage holding capacitor included in HV therapy module 83 when the high-voltage pacing output configuration is selected based on the capture threshold testing. When pacing pulses are delivered in the high-voltage pacing output configuration, the high voltage holding capacitor of HV therapy module 83 may be charged in anticipation of a required pacing therapy. Prior to a first pacing pulse, the charge on a high voltage holding capacitor, e.g., capacitor 210 of FIG. 9, may be topped off to the programmed pacing pulse voltage amplitude. For example, top-off charging may be enabled up to one second prior to delivering a pacing pulse, or upon anticipating a need for delivering a pacing pulse, which may be the first pacing pulse of a series of pulses delivered for capture threshold testing, ATP, post-shock pacing, bradycardia pacing or tachyarrhythmia induction. As such, HV therapy module 83 may be enabled by control module 80 to perform capacitor charge top-off charging at times that a shock therapy may not be needed and in response to selecting the high voltage pacing output configuration. In this way, delivery of the pacing pulse energy from the HV therapy module is readily available upon scheduling a pacing pulse.

After enabling a selected pacing output configuration and corresponding pacing control parameters (at blocks 106 and 108 or at blocks 114 and 116 or at blocks 120 and 124), ICD 14 delivers pacing pulses as needed according to programmed pacing therapies or tachyarrhythmia induction protocols at block 130. Bradycardia pacing pulses, ATP pulses, asystole pacing pulses post-shock or during atrio-ventricular conduction block, entrainment pulses prior to T-shock delivery for tachyarrhythmia induction, burst pulses for tachyarrhythmia induction, or other pacing therapies or tachyarrhythmia induction sequences may be delivered according to programmed pacing control parameters, including timing intervals such as ventricular lower rate intervals, atrio-ventricular pacing intervals, ATP inter-pulse intervals, etc., using the selected pacing output configuration.

It is contemplated that in some examples, the pacing parameters set at one of blocks 108, 116 or 124 may include enabling and/or disabling one or more pacing therapies. For example, if the high-voltage pacing output configuration is enabled with a relatively high pacing amplitude that is tolerable for short intervals of time but intolerable by the patient for relatively longer periods of time, ATP therapy may be enabled which is of relatively short duration. Asystole pacing post-shock or during atrioventricular conduction block, which can be life-saving, may also (or alternatively) be enabled.

Bradycardia pacing, which can be delivered over extended periods of time, may be disabled. As such, setting HV pacing parameters at block 124 by control module 80 may include enabling ATP therapy and/or asystole pacing and disabling bradycardia pacing.

Asystole pacing may be provided when an R-wave is not sensed for an asystole back up pacing interval, e.g., 1.5 to 2 seconds. On the other hand, if the low-voltage, single pulse or low-voltage fused pacing output configuration is enabled, bradycardia pacing and/or other pacing therapies that may extend over relatively long periods of time (e.g., minutes or hours) may be enabled at block 108 or 116, in addition to ATP and asystole pacing or other short duration or life-saving pacing therapies if the patient is highly tolerant of the extra-cardiovascular pacing pulses delivered by LV therapy module 85. If the selected low-voltage pacing output configuration causes patient discomfort, bradycardia pacing may be disabled at block 108 or 116 with ATP and/or asystole pacing therapy enabled.

It is recognized that in some patients reliable capture of heart 26 may still not be achieved even using the HV pacing output configuration. Even if capture is achieved, a relatively high pacing capture threshold may exceed a tolerable level of pain caused by extra-cardiac capture of surrounding skeletal muscle. In this case, the HV pacing output configuration may be disabled such that extra-cardiovascular pacing therapies are not delivered by ICD 14. In some cases, re-positioning of lead 16 and/or selection of a different pacing electrode vector may enable capture at a comfortable pacing output level.

Although FIG. 8 is described as including two low-voltage pacing output configurations, the techniques described may be utilized with only a single low-voltage pacing output configuration (e.g., only the low-voltage single pulse pacing output configuration or only the low-voltage fused pacing output configuration) or with more than two low-voltage pacing output configurations. Likewise, there may be instances in which the techniques can be used with more than one high-voltage pacing output configuration.

Figure 9:
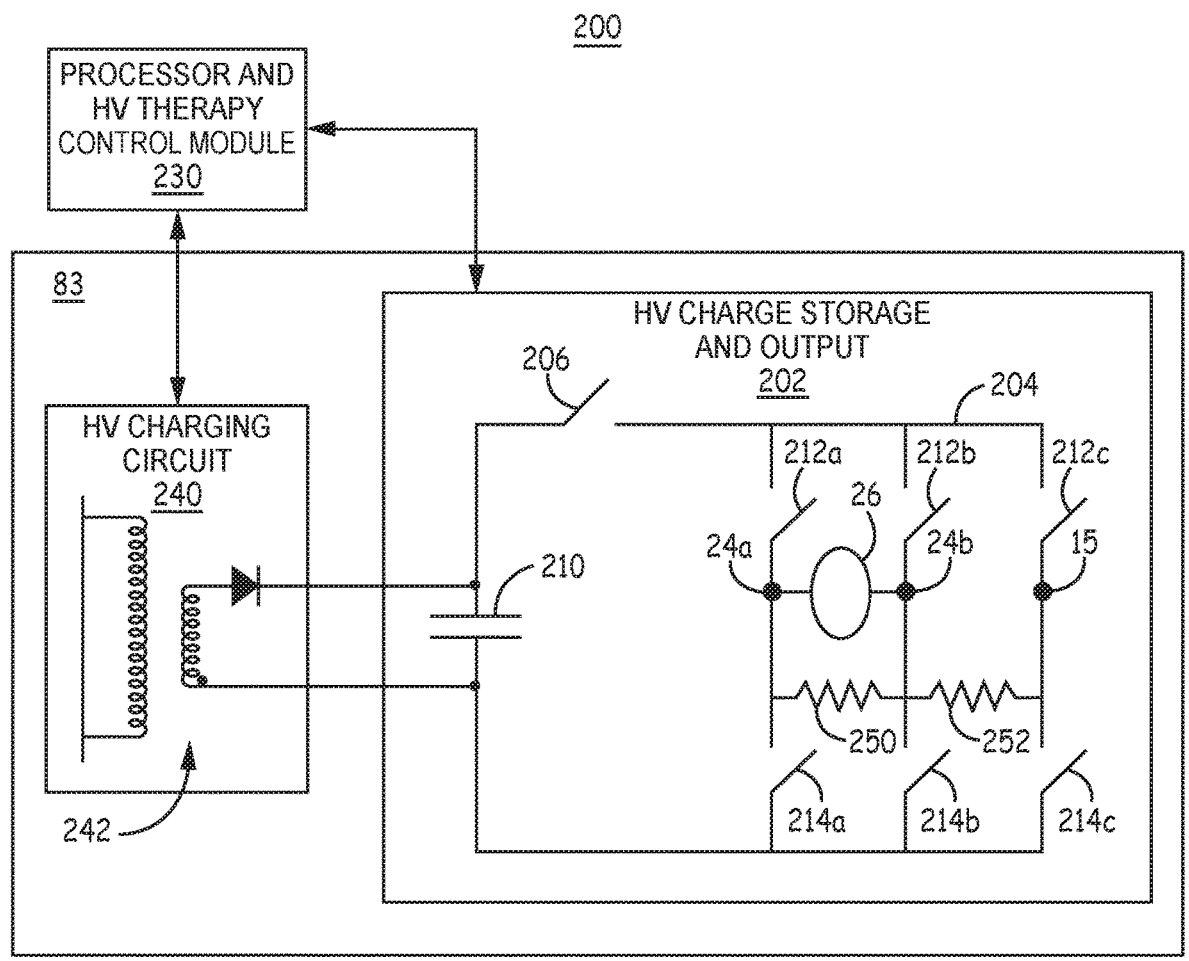
FIG. 9 is schematic diagram of a HV therapy module coupled to a processor and HV therapy control module of the ICD of FIGS. 1A-2C according to one example.

FIG. 9 is schematic diagram 200 of HV therapy module 83 coupled to a processor and HV therapy control module 230. HV therapy module 83 includes a HV charging circuit 240 and a HV charge storage and output module 202. Processor and HV therapy control module 230 may be included in control module 80 for controlling HV charging circuit 240 and HV charge storage and output module 202. HV charge storage and output module 202 includes a HV capacitor 210 coupled to switching circuitry 204 via a pulse width control switch 206 for coupling the HV capacitor 210 to electrodes 24a, 24b and/or housing 15 to deliver a desired HV electrical stimulation pulse to the patient's heart 26. HV capacitor 210 is shown as a single capacitor, but it is recognized that a bank of two or more capacitors or other energy storage devices may be used to store energy for producing electrical signals delivered to heart 26. In one example, HV capacitor 210 is a series of three capacitors having an effective capacitance of 148 microfarads.

Switching circuitry 204 may be in the form of an H-bridge including switches 212a-212c and 214a-214c that are controlled by signals from processor and HV control module 230. Switches 212a-212c and 214a-214c may be implemented as silicon-controlled rectifiers (SCRs), insulated-gate bipolar transistors (IGBTs), metal-oxide-semiconductor field-effect transistors (MOSFETs), and/or other switching circuit components.

When control module 80 determines that delivery of an electrical stimulation pulse from HV therapy module 83 is needed, switching circuitry 204 is controlled by signals from processor and HV therapy control module 230 to electrically couple HV capacitor 210 to a therapy delivery vector to discharge capacitor 210 across the vector selected from electrodes 24a, 24b and/or housing 15. The selected electrodes 24a, 24b and/or housing 15 are coupled to HV capacitor 210 by opening (i.e., turning off or disabling) and closing (i.e., turning on or enabling) the appropriate switches of switching circuitry 204 to pass a desired electrical signal to the therapy delivery electrode vector. The electrical signal may be a monophasic, biphasic or other shaped CV/DF shock signal for terminating a ventricular tachyarrhythmia when VT or VF is detected.

For example, when a bi-phasic CV/DF shock is needed, one of switches 212a, 212b and 212c may be closed simultaneously with one of switches 214a, 214b and 214c without closing both of the "a," "b" or "c" switches across a given electrode 24a, 24b or housing 15, respectively, at the same time. To deliver a biphasic pulse using electrode 24a and housing 15, for instance, switch 212a and 214c may be closed to deliver a first phase of the biphasic pulse. Switches 212a and 214c are opened after the first phase, and switches 212c and 214a are closed to deliver the second phase of the biphasic pulse. Switches 212b and 214b remain open or disabled in this example with electrode 24b not selected or used in the therapy delivery vector. In other examples, electrode 24B may be included instead of electrode 24A or simultaneously activated with electrode 24A by closing switch 212b during the first phase and closing switch 214b in the second phase of the illustrative biphasic pulse.

When control module 80 enables the high-voltage pacing output configuration, capacitor 210 is charged to a programmed pacing pulse amplitude by HV charging circuit 240 under the control of processor and HV therapy control module 230. Switches 212a-212c and 214a-214c are controlled to be open or closed by processor and HV therapy control module 230 at the appropriate times for delivering a monophasic, biphasic or other desired pacing pulse by discharging capacitor 210 across the pacing load presented by heart 26 and a selected pacing electrode vector. The capacitor 210 is coupled across the selected pacing electrode vector for the programmed pacing pulse width.

In the example shown, the high-voltage pacing output configuration may be enabled using electrodes 24a and 24b carried by lead 16. Housing 15 may be unused by holding switches 212c and 214c open. Depending on the implant location of ICD 14 and lead 16 and the resulting electrical stimulation delivery vector between the housing 15 and one or both of electrodes 24a and 24b, greater recruitment of skeletal muscle may occur when housing 15 is included in the pacing electrode vector. A larger volume of skeletal muscle tissue may lie along a vector extending between the distal portion 25 of lead 16 and housing 15 than along a vector extending between the two electrodes 24a and 24b along lead distal portion 25. In the example configurations of FIGS. 1A-2C, for example, a pacing pulse may be delivered between the electrodes 24a and 24b to limit skeletal muscle recruitment compared to a pacing electrode vector that includes housing 15. In other electrode configurations and implant locations, the electrodes used to deliver extra-cardiovascular pacing pulses by HV therapy module 83 may be selected to provide a delivery vector that minimizes the volume of skeletal muscle included in the pacing electrode vector while directing sufficient energy to the heart 26 for capturing and pacing the heart.

A biphasic pacing pulse, such as pulse 70 of FIG. 7, may be delivered between electrodes 24a and 24b by producing a positive-going portion by closing switch 212a and switch 214b for a first portion 70a of pulse width 74 to discharge HV capacitor 210 across electrodes 24a and 24b through heart 26. The switches 212a and 214b are opened, and switches 212b and 214a are closed to deliver the negative-going phase, portion 70b, of the biphasic pacing pulse 70. All switches of switching circuitry 204 are opened upon expiration of the pulse width 74, e.g., based on a time out of a pulse width timer included in processor and HV therapy control module 230.

Between pacing pulses, as long as VT or VF are not being detected, the HV capacitor 210 is charged to the programmed pacing pulse amplitude. HV charging circuit 240 receives a voltage regulated signal from power source 98 (FIG. 5). HV charging circuit 240 includes a transformer 242 to step up the battery voltage of power source 98 in order to achieve charging of capacitor 210 to a voltage that is much greater than the battery voltage. Charging of capacitor 210 by HV charging circuit 240 is performed under the control of processor and HV therapy control 230, which receives feedback signals from HV charge storage and output module 202 to determine when capacitor 210 is charged to a programmed voltage. A charge completion signal is passed to HV charging circuit 240 to terminate charging by processor and HV therapy control module 230. One example of a high voltage charging circuit and its operation is generally disclosed in U.S. Pat. No. 8,195,291 (Norton, et al.), incorporated herein by reference in its entirety.

While not shown in the example of FIG. 9, in other examples electrodes 28A, 28B and 30 may be selectively coupled to HV therapy module 83 via additional switches included in switching circuitry 204 so that HV pacing pulses may be delivered using a pacing electrode vector that includes electrodes 28A, 28B and/or 30.

HV charge storage and output module 202 is shown to include a shunt resistance 250 in parallel to the pacing load shown schematically as heart 26 when electrodes 24A and 24B are selected as the anode and cathode (or cathode and anode, respectively) of the pacing electrode vector. It is recognized that a shunt resistance may be provided in parallel to the pacing load for any selected pacing electrode vector, for example shunt resistance 252 is shown schematically if the pacing electrode vector includes electrode 24B and housing 15. Likewise a shunt resistance may be provided in parallel to the pacing load when the pacing electrode vector includes electrode 24A and housing 15.

Switches 212a-212c and switches 214a-214c may require a minimum current flow to hold them closed (i.e., ON or enabled) for passing current as capacitor 210 is discharged. This minimum current may be on the order of approximately 10 milliamps.

Depending on the pacing load impedance and other conditions, the electrical current passing through enabled switches of switches 212a-212c and 214a-214c may fall below the minimum current required to keep the switches closed as capacitor 210 is discharged across a selected pacing vector. If the current passing through a respective switch falls below the minimum current required to keep the switch closed, the switch may open (or become disabled) causing premature truncation of the pacing pulse, which could result in loss of capture. As such, a minimum pacing pulse voltage amplitude may be set for the high-voltage pacing output configuration in order to reduce the likelihood of the electrical current produced during capacitor discharge falling below the minimum current required to maintain a stable state of enabled switches of switching circuitry 204 during a programmed pacing pulse width.

The shunt resistance 250 or 252 may be a variable resistance that is set to match a pacing electrode vector impedance so that the load across heart 26 using a selected pacing electrode vector matches the shunt resistance. In this way, current through the switching circuitry 204 may be maintained at or above a minimum current required to maintain a stable state of enabled switches of switching circuitry 204 during the pacing pulse. If the shunt resistance 250 is higher than the pacing electrode vector impedance across heart 26, the electrical current applied to selected switches of switching circuitry 204 may fall below the minimum required to maintain the enabled state of the selected switches.

If the shunt resistance 250 or 252 is lower than the pacing electrode vector impedance, current produced by discharging capacitor 210 may be shunted away from the pacing load, e.g., the pacing electrode vector between electrodes 24a and 24b and heart 26, resulting in less energy delivered to heart 26, which may result in loss of capture. Accordingly, processor and HV therapy control module 230 may be configured to retrieve a pacing electrode vector impedance measurement from impedance measurement module 90 and set the shunt resistance 250 (or 252) to match the pacing electrode vector impedance.

In other examples, a minimum voltage charge of capacitor 210 may be set to provide the minimum current required to maintain an enabled state of selected switches of switching circuitry 204, but pacing energy may be intentionally shunted away from the pacing load including heart 26 in order to reduce the delivered pacing pulse energy. If the pacing amplitude capture threshold is below the minimum voltage amplitude required to maintain the minimum current to keep switches 212a-212c and 214a-214c on when they are enabled by processor and HV therapy control module 230, the energy delivered across the pacing electrode vector may be reduced by setting the variable shunt resistance 250

(or 252) to a value that is less than the pacing electrode vector impedance. This current shunting may reduce skeletal muscle recruitment caused by the extra-cardiovascular pacing pulse while still providing effective capture of heart 26.

Since the range of pacing load impedances and pacing voltage amplitudes may vary between patients and at different times within a patient, a variable shunt resistance may be provided to enable selection of the appropriate resistance for shunting the required current through the switching circuitry. It is contemplated, however, that in some examples a fixed resistance shunt may be provided. For example, the resistance needed to shunt current to the switching circuit when the pacing load impedance is high may still shunt some current to the switching circuitry when the pacing load impedance is relatively lower. An optimal value for a fixed resistance shunt may be determined based on empirical data, e.g., typical pacing load impedances and pacing pulse voltage amplitudes used clinically.

Figure 10:
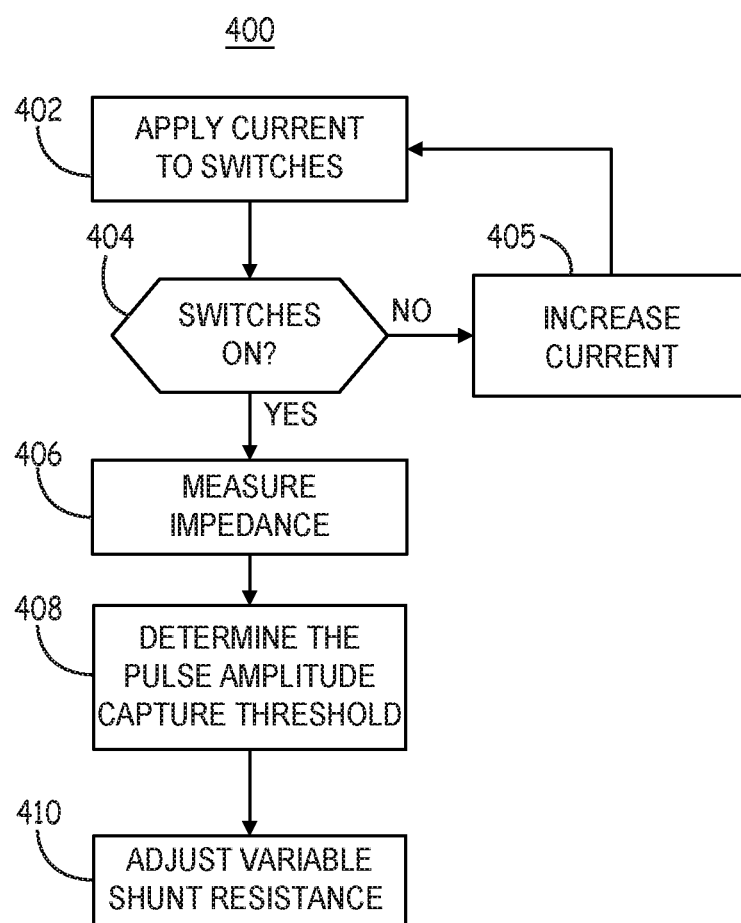
FIG. 10 is a flow chart of one method that may be performed by the ICD of FIGS. 1A-2C for enabling a high-voltage, pacing output configuration.

FIG. 10 is a flow chart 400 of one method that may be performed by ICD 14 as part of enabling a high-voltage, pacing output configuration at block 120 of FIG. 8. At block 402, processor and HV therapy control module 230 may control the HV therapy module 83 to apply electrical current to switching circuitry 204. Current is applied to selected ones of switches 212a-212c and 214a-214c in order enable or activate the selected switches to select a desired pacing electrode vector. A minimum electrical current is required in order to maintain an enabled switch of switching circuitry 204 in the ON or closed state. If the current is too low, the switch may open.

At block 404, processor and HV therapy control module 230 may receive a feedback signal from switching circuitry 204 indicating that the selected switches are ON or enabled. If the selected switches of switching circuitry 204 are not enabled by the current applied at block 402, the applied electrical current may be increased at block 405. The feedback signal may be a sampled electrical current signal or a sampled impedance signal in switching circuitry 204.

Once the desired switches are enabled, an impedance measurement may be made at block 406 by impedance measurement module 90 under the control of processor and HV therapy control module 230. In some examples, the variable shunt resistance 250 is adjusted to match the measured pacing electrode vector impedance at block 410. By setting the variable shunt resistance 250 to match the pacing load resistance, the enabled switches of switching circuitry 204 will remain enabled by the required minimum current when capacitor 210 is discharging across the pacing load. In another example, the electrical current on an output line to the pacing load from HV charge storage and output module 202 is sampled. If the sampled electrical current is zero, the shunt resistance 250 is decreased.

In other examples, the control module 80 may control high voltage therapy module 83 to perform a pacing amplitude threshold test at block 408. If the minimum charge voltage of capacitor 210 required to maintain a minimum electrical current applied to enable switches of switching circuitry 204 is greater than the pacing amplitude capture threshold, the variable shunt resistance 250 may be adjusted to a resistance that is less than the pacing load impedance. A shunt resistance that is lower than the pacing load resistance will shunt current away from the pacing load and thereby reduce energy delivered across the pacing electrode vector to the patient's heart. For example, a minimum 10 V charge of capacitor 210 may be required in order to apply and maintain the minimum electrical current needed to keep selected switches of switching circuitry 204 enabled. During a threshold test, if a pacing pulse having the minimum 10 V amplitude and a relatively short pulse width, e.g., 2 ms, captures the patient's heart 26, the pulse amplitude capture threshold may be less than 10 V and even more likely less than 10 V when a longer pulse width is used, e.g., 10 ms. A lower energy pacing pulse may be tested by decreasing the variable shunt resistance so that some pacing energy is shunted across shunt resistor 250 rather than across the pacing electrode vector. If capture still occurs, the pacing capture threshold is less than the minimum voltage charge of capacitor 210 that is required to produce the minimum current for enabling the switches 212a-212c and 214a-214c of circuitry 204.

If this is the case, the variable shunt resistance 250 may be adjusted at block 410 to a resistance that is less than the pacing electrode vector impedance to reduce the energy delivered to heart 26 (and surrounding skeletal muscle) when capacitor 210 is charged to the minimum voltage and discharged across the pacing load. If the pulse amplitude capture threshold is equal to or greater than the minimum charge voltage of capacitor 210, the variable shunt resistance may be set to match the pacing electrode vector impedance. As such, the variable shunt resistance 250 provided in parallel to the pacing electrode vector may be adjusted by processor and HV control module 230 based on the pacing electrode vector impedance (e.g., matching the pacing electrode vector impedance). In other examples, the variable shunt resistance 250 is set based on pacing electrode vector impedance and the pulse amplitude capture threshold. When the pulse amplitude capture threshold is equal to or greater than the minimum charge of capacitor 210 required to maintain a minimum required current to switches of switching circuitry 204, the variable shunt resistance 250 may be set to match the pacing electrode vector impedance. When the pulse amplitude capture threshold is less than the minimum required charge of capacitor 210, the variable shunt resistance 250 may be set to a value that is less than the pacing electrode vector impedance.

In some examples, some or all of the process shown by flow chart 400 including measuring impedance at block 406 and adjusting the variable shunt resistance based on the pacing electrode vector impedance at block 410 is performed for every pacing pulse delivered by ICD 14 when the high-voltage, pacing output configuration is enabled. In this way, the variable shunt resistance may be adjusted on a pulse-by-pulse basis to match (or in some cases be less than) the pacing load resistance for every pacing pulse and thereby minimize the likelihood of any of the switches of switching circuitry 204 being inadvertently disabled due to low current flow, which could result in a non-delivered or prematurely truncated pacing pulse and loss of capture.

Figure 11:
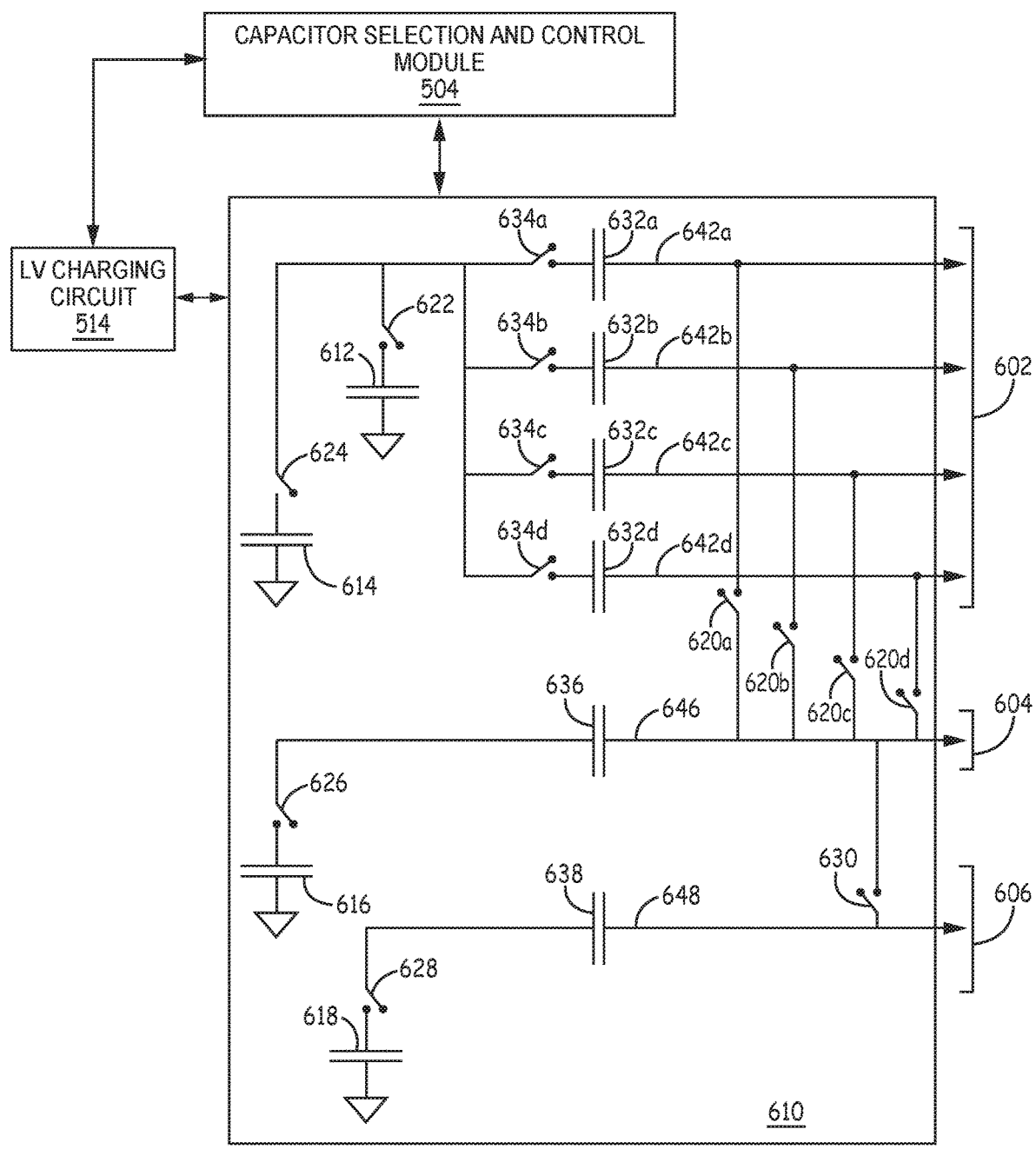
FIG. 11 is a conceptual diagram of a LV therapy module of the ICD of FIGS. 1A-2C according to one example.

FIG. 11 is a conceptual diagram of LV therapy module 85 according to one example. LV therapy module 85 may include a capacitor selection and control module 504, a LV charging circuit 514, and a capacitor array 610. Capacitor array 610 may include multiple holding capacitors 612, 614, 616 and 618 that can each be charged by LV charging circuit 514 to a programmed pacing pulse amplitude. The holding capacitors 612, 614, 616 and 618 are coupled to a respective output capacitor 632a-632d (collectively 632), 636, or 638 via respective switches 622, 624, 626, and 628 to deliver low-voltage pacing pulses. Each of holding capacitors 612, 614, 616 and 618 has a capacitance that is less than the effective capacitance of high voltage capacitor 210 of HV therapy module 83. For example each of holding capacitors 612, 614, 616 and 618 may have a capacitance of up to 6 microfarads, up to 10 microfarads, up to 20 microfarads or other selected capacitance, but all have a capacitance significantly less than the effective capacitance of high voltage capacitor 210.

Power source 98 (FIG. 5) may provide regulated power to LV charging circuit 514. LV charging circuit 514 may be controlled by a state machine in capacitor selection and control module 504 to charge all or selected holding capacitors 612, 614, 616 and 618 using a multiple of the battery voltage of power source 98, e.g., four times the battery voltage. LV charging circuit 514 charges capacitors 612, 614, 616 and/or 618 as needed for delivering low voltage pacing pulses, either single pacing pulses or composite pacing pulses, according to a selected low-voltage pacing output configuration.

In some examples, the LV therapy module 85 includes three pacing channels 602, 604 and 606. Each pacing channel is capable of producing a single pacing pulse when a respective holding capacitor 612, 616 or 618 is discharged across an output capacitor 632, 636, or 638, respectively. Pacing channel 602 includes a back-up holding capacitor 614 that may be used for delivering back-up pacing pulses, e.g., when a low-voltage, single pulse pacing output configuration is selected. Back-up holding capacitor 614 may be used to deliver an individual pulse of a composite pacing pulse when the low-voltage, fused pacing output configuration is selected.

Depending on the number of extra-cardiovascular electrodes coupled to ICD 14, one or more channels may include multiple selectable output signal lines. For example, channel 602 is shown in this example to include multiple selectable pacing output signal lines 642a-642d that may be selectively coupled to holding capacitor 612 and back-up holding capacitor 614 via closure of one or more of electrode selection switches 634a-634d. For example, multiple electrodes carried by lead 16 may be coupled to pacing channel 602 and a pacing electrode vector may be selected from the multiple electrodes by closing certain ones of switches 634a-634d.

Pacing channels 604 and 606 are shown having single output signal lines 646 and 648 that are coupled to respective holding capacitors 616 and 618 via respective switches 626 and 628. In other examples, all three pacing channels 602, 604 and 606 may be provided with a single output signal line or with multiple output signal lines to enable selection of a pacing electrode vector from among multiple extra-cardiovascular electrodes coupled to ICD 14, e.g., any of electrodes 24A, 24B, 28A, 28B, and 30 of lead 16 shown in FIGS. 1A-4.

When the low-voltage, single channel pacing output configuration is enabled by control module 80, any one of the pacing channels 602, 604 and 606 may be used to deliver a single pacing pulse. The single pacing pulse may be delivered by discharging one of the holding capacitors 612, 614, 616 or 618 across a selected pacing electrode vector via a respective output capacitor 632, 636 or 638 when a respective switch 622, 624, 626 or 628 is closed. The output line 642a, 642b, 642c, or 642d used to deliver pacing current from pacing channel 602 may be selected via a respective electrode selection switch 634a-634d. The switches 622, 624, 626 or 628 that enable discharge of a holding capacitor 612, 614, 616, or 618, respectively, may be enabled by capacitor selection and control module 504 at the appropriate time when a pacing pulse is needed and maintained in an active, enabled state until the single pacing pulse width is expired.

For example, pacing channel 602 may be coupled to pace/sense electrode 28A, pacing channel 604 may be coupled to pace/sense electrode 28B and pacing channel 606 may be coupled to pace/sense electrode 30 in the examples shown in FIGS. 1A-2C. If additional pace/sense electrodes are available, or if defibrillation electrodes 24A and 24B are also used for pacing, the additional electrodes or defibrillation electrodes 24A and 24B may be coupled to a pacing output channel, such as channel 602, to provide multiple selectable pacing electrode vectors.

When control module 80 selects the low-voltage, fused pacing output configuration, the pacing channels 602, 604 and 606 are tied together by switches 620a-620d and 630 to enable individual pulses to be delivered across a selected pacing electrode vector from a single output signal line 646. For example, control module 80 may enable the low-voltage, fused pacing output configuration by activating switches 620a-620b and 630 to tie pacing output lines 642a-642d and pacing output line 648 to pacing channel 604. Control module 80 controls capacitor selection and control module 504 to enable pacing channel switches 622, 624, 626 and 628 (and at least one electrode selection switch 634a-634d of pacing channel 602) in a sequential manner to couple a respective holding capacitor 612, 614, 616 or 618 to output signal line 646 to deliver a sequence of fused, individual pulses to produce a composite pacing pulse.

In various examples, depending on the particular pacing channel and lead and electrode configuration used with ICD 14, some electrode selection switches shown in FIG. 11 may not be required. Furthermore it is recognized that less than four holding capacitors or more than four holding capacitors may be included in a capacitor array 610 for use in delivering a sequence of fused pacing pulses when the low-voltage, fused pacing output configuration is selected.

Capacitor selection and control module 504 selects which holding capacitors 612, 614, 616 and 618 are coupled to output line 646 and in what sequence by controlling respective switches 622, 624, 626 and 628. A sequence of pulses may be delivered to produce a composite pacing pulse by sequentially discharging holding capacitors 612, 614, 616 and 618 one at a time (or one combination at a time) across a respective output capacitor 632, 636 and 638 by sequentially enabling or closing the respective switches 622, 624, 626 and 628. For example, at least two of holding capacitors 612, 614, 616 and 618 are sequentially discharged to produce a composite pacing pulse produced by at least two fused individual pulses. Output line 646 may be electrically coupled to a pacing cathode electrode carried by lead 16 and a return anode electrode carried by lead 16 (or housing 15) may be coupled to ground. The pacing cathode electrode and return anode electrode may correspond to electrodes 28A and 28B as shown in FIG. 3 or FIG. 4 in one example, or any pacing electrode vector selected from electrodes 24A, 24B, 28A, 28B, 30 and/or housing 15 shown in FIG. 1A through FIG. 4.

In some examples, a low-voltage, fused pacing pulse is delivered by delivering an individual pulse from pacing channel 604 and 606 sequentially followed by a third, longer individual pulse delivered by pacing channel 602 by discharging both capacitors 612 and 614 simultaneously. The first two individual pulses may be 2.0 ms in pulse width and the third pulse may be 4.0 ms in pulse width for a composite pacing pulse width of 8 ms. The higher capacitance of the parallel capacitors 612 and 614 allows for the third individual pulse to be longer in pulse width while maintaining a pulse amplitude that successfully captures the heart. All three individual pulses are delivered via output line 646 because output configuration switches 620 and 630 are enabled for the low-voltage fused pacing output configuration.

In other examples, selected ones of holding capacitors 612, 614, 616, and 618 are discharged sequentially. For example, to deliver a composite pacing pulse, such as pulse 50 in FIG. 6, each of holding capacitors 612, 614, 616 and 618 are discharged for 2.0 ms, one at a time in fused succession to deliver a composite pacing pulse having a pulse width of 8 ms. Each holding capacitor 612, 614, 616 and 618 is charged to the pacing pulse amplitude set for the low-voltage, fused pacing output configuration, e.g., 8 V or less, which may be based on a fused pacing capture threshold test and the maximum available pulse amplitude of the LV therapy module 85. Other examples of a LV therapy module and composite pacing pulse techniques that may be used in conjunction with the techniques disclosed herein are generally disclosed in the above-incorporated U.S. Pat. Application 62/262,412 and the corresponding US. Pat. Application Publication No. 2017/0157399 (filed on the same day herewith).

Figure 12:
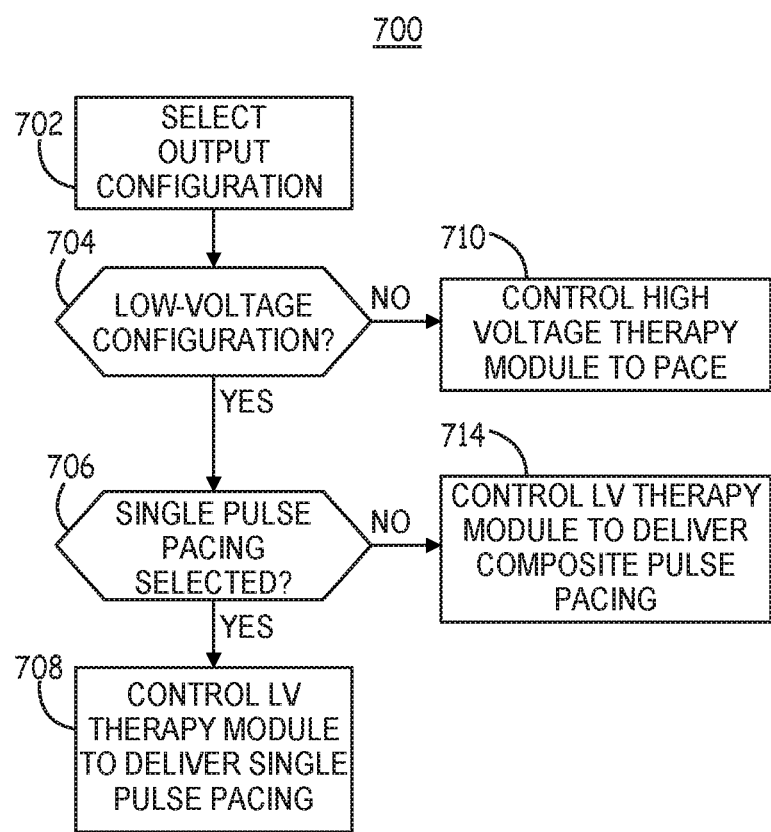
FIG. 12 is a flow chart of a method performed by an ICD according to one example.

FIG. 12 is a flow chart 700 of a method performed by ICD 14 for selecting one of the pacing output configurations described herein for delivering extra-cardiovascular pacing pulses by the therapy delivery module 84. The method of flow chart 700 may be performed upon initial implant of ICD 14, periodically thereafter, and/or upon determining a need for pacing pulse delivery. At block 702, control module 80 selects a pacing output configuration. Control module 80 selects the pacing output configuration from among at least a first low-voltage, pacing output configuration and a high-voltage pacing output configuration. In some examples, control module 80 selects from a single-pulse pacing output configuration of the LV therapy module 85, a composite-pulse pacing output configuration of the LV therapy module 85 and a high-voltage pacing output configuration of the HV therapy module 83. In some examples, control module 80 selects the pacing output configuration based on a programmed selection, and in other examples control module 80 actively selects the pacing output configuration based on tests performed by ICD 14, e.g., based on capture threshold testing as described in conjunction with FIG. 8 above.

If the selected pacing output configuration is not a low-voltage, pacing output configuration, "no" branch of block 704, control module 80 controls the HV therapy module 83 to deliver one or more extra-cardiovascular pacing pulses according to a pacing protocol at block 710. HV therapy module 83 may be controlled to charge the HV capacitor 210 (FIG. 9) to a pacing pulse amplitude via transformer 242 and enable discharging of the HV capacitor 210 via switching circuitry 204 to deliver the extra-cardiovascular pacing pulse(s). The switches included in switching circuitry 204 may be maintained in an active state for a pacing pulse width by setting a variable shunt resistance 250/252 as described above in conjunction with FIG. 10. In some cases the HV capacitor 210 is charged to a minimum voltage required to provide the electrical current required to maintain selected switches of the switching circuitry 204 in an active (closed) state for the duration of the pacing pulse width. In other examples, the HV capacitor 210 may be charged to a pacing pulse voltage amplitude that is greater than the minimum voltage required to provide current to maintain selected switches in an active state but less than the voltage required to generate a defibrillation or cardioversion shock having a shock energy that meets the patient's defibrillation threshold.

If a low-voltage pacing output configuration is selected at block 704, and the selected configuration is a single-pulse pacing configuration, "yes" branch of block 706, the control module 80 controls the LV therapy module 85 to deliver one or more single-pulse, extra-cardiovascular pacing pulses at block 708, according to a pacing protocol.

The single-pulse pacing pulses are delivered by charging one holding capacitor of the LV therapy module 85 to a pacing pulse voltage amplitude and discharging the holding capacitor for a pacing pulse width, which may be the maximum pacing pulse width available from the LV therapy module 85, as described above in conjunction with FIG. 8.

If a low-voltage, pacing output configuration is selected, but not the single-pulse pacing configuration, "no" branch of block 706, control module 80 controls the LV therapy module 85 to deliver composite pulse pacing at block 714. One or more composite pacing pulses, each including two or more fused individual pulses delivered within the composite pacing pulse width, are delivered according to a pacing therapy protocol. Each composite pacing pulse is delivered by charging at least two different holding capacitors of LV therapy module 85 and discharging the at least two different holding capacitors on a common output line sequentially in time as described above in conjunction with FIG. 11. In some examples, the control module 80 may be configured to select from the high-voltage pacing output configuration of HV therapy module 83 and a single low-voltage pacing output configuration, which may be either the single-pulse pacing output configuration or the fused pacing output configuration of LV therapy module 85.

ICD 14 is configured to select the pacing output configuration from among at least a first low-voltage pacing output configuration and a high-voltage, pacing output configuration to provide extra-cardiovascular pacing to a patient's heart in a manner that conserves ICD battery longevity, minimizes patient discomfort, while promoting reliable capture of the patient's heart by delivered pacing pulses.

Thus, a method and apparatus for delivering cardiac pacing pulses using an extra-cardiovascular ICD system have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. An extra-cardiovascular implantable cardioverter defibrillator (ICD) comprising:
   a high voltage therapy module including:
     a high voltage capacitor having a first capacitance;
     a high voltage charging circuit configured to charge the high voltage capacitor; and
     first switching circuitry configured to couple the high voltage capacitor across extra-cardiovascular electrodes coupled to the ICD;
   a low voltage therapy module including:
     a plurality of low voltage capacitors each having up to a second capacitance that is less than the first capacitance;
     a low voltage charging circuit configured to charge the plurality of low voltage capacitors; and
     second switching circuitry configured to selectively couple the plurality of low voltage capacitors to the extra-cardiovascular electrodes coupled to the ICD; and a control module coupled to the high voltage therapy module and the low voltage therapy module and configured to:
control at least one of the low voltage therapy module or the high voltage therapy module to perform a pacing capture test;
based on the pacing capture test, select a pacing output configuration from among at least a low-voltage pacing output configuration of the low voltage therapy module and a high-voltage pacing output configuration of the high voltage therapy module;
control a respective one of the low voltage therapy module and the high voltage therapy module to deliver extra-cardiovascular pacing pulses in the selected one of the low-voltage pacing output configuration or the high-voltage pacing output configuration via the extra-cardiovascular electrodes.

2. The ICD of claim 1, further comprising a sensing module configured to receive a cardiac electrical signal via the extra-cardiovascular electrodes, wherein the control module is configured to control at least one of the low voltage therapy module or the high voltage therapy module to perform the pacing capture test by:
controlling the low voltage therapy module to deliver at least one pacing pulse in a first low-voltage pacing output configuration;
determining from the cardiac electrical signal that the at least one pacing pulse captures a patient's heart;
determining that first pacing capture threshold criteria are met in response to determining that the at least one pacing pulse captures the patient's heart; and
select the pacing output configuration by selecting the pacing output configuration as the first low-voltage pacing output configuration in response to the first pacing capture threshold criteria being met.

3. The ICD of claim 2, wherein the control module is configured to determine that the first capture threshold criteria are met by determining that at least one pacing pulse delivered using the first low-voltage pacing output configuration captures the patient's heart when the at least one pacing pulse has a pulse amplitude that is at least a safety margin less than a maximum pacing pulse amplitude producible by the low voltage therapy module.

4. The ICD of claim 2, wherein the control module is further configured to select the pacing output configuration by selecting the high-voltage pacing output configuration in response to determining that the first pacing capture threshold criteria are not met.

5. The ICD of claim 2, wherein the control module is further configured to select the pacing output configuration by:
in response to determining that the first pacing capture threshold criteria are not met, controlling the low voltage therapy module to deliver at least one pacing pulse in a second low-voltage pacing output configuration of the low voltage therapy module;
determining from the cardiac electrical signal that the at least one pacing pulse delivered in the second low-voltage pacing output configuration captures the patient's heart;
determining that second pacing capture threshold criteria are met in response to determining that the at least one pacing pulse delivered in the second low-voltage pacing output configuration captures the patient's heart; and
selecting the pacing output configuration as the second low-voltage pacing output configuration in response to the second pacing capture threshold criteria being met and the first pacing capture threshold criteria being unmet.

6. The ICD of claim 5, wherein controlling the low voltage therapy module to deliver extra-cardiac pacing pulses in the first low-voltage pacing output configuration comprises enabling the low voltage therapy module to deliver a single-pulse pacing pulse having a pulse width up to a maximum pulse width, and
wherein controlling the low voltage therapy module to deliver extra-cardiovascular pacing pulses in the second low-voltage pacing output configuration comprises enabling the low voltage therapy module to deliver a composite pacing pulse comprising at least two fused individual pulses produced by discharging at least two different capacitors of the plurality of low voltage capacitors in sequence, wherein the composite pacing pulse has a pulse width that is longer than the maximum pulse width of the single-pulse pacing pulse.

7. The ICD of claim 5, wherein the control module is configured to determine that the second capture threshold criteria are met by determining from the cardiac electrical signal that at least one composite pacing pulse delivered using the second low-voltage pacing output configuration captures the patient's heart when the at least one composite pacing pulse has a pulse amplitude that is at least a safety margin less than a maximum pacing pulse amplitude producible by the low voltage therapy module and has a composite pacing pulse width comprising at least two fused individual pulses.

8. The ICD of claim 5, wherein the control module is further configured to select the pacing output configuration by selecting the high-voltage pacing output configuration in response to determining that the second pacing capture threshold criteria are not met.

9. The ICD of claim 1, wherein the control module is further configured to set a plurality of pacing control parameters for the selected pacing output configuration when the selected pacing output configuration is the low-voltage pacing output configuration by:
determining a pacing amplitude capture threshold for the low-voltage pacing output configuration;
setting a pacing pulse amplitude by adding a safety margin to the pacing amplitude capture threshold; and
setting a pulse width to a maximum pulse width available for a single-pulse pacing pulse.

10. The ICD of claim 1, wherein the control module is further configured to set a composite pacing pulse width to include at least two fused individual pacing pulses when the selected pacing output configuration is the low-voltage pacing output configuration.

11. The ICD of claim 1, wherein:
the high voltage therapy module comprises a variable shunt resistance;
the control module is configured to control the high voltage therapy module to deliver the extra-cardiovascular pacing pulses in the high voltage pacing output configuration when the high voltage pacing output configuration is selected by:
applying an electrical current to enable the first switching circuitry;
determining an impedance of a pacing electrode vector selected from the extra-cardiovascular electrodes; and
setting the variable shunt resistance in parallel to a pacing load of the pacing electrode vector based on the impedance.

12. The ICD of claim 11, wherein the control module is configured to set the variable shunt resistance equal to the impedance.

13. The ICD of claim 11, wherein the control module is further configured to:
control the high voltage therapy module to perform a test to determine a pacing amplitude capture threshold;
determine that the pacing amplitude capture threshold is less than a minimum voltage charge of the high voltage capacitor required to produce the electrical current to enable the first switching circuitry; and
set the variable shunt resistance to be less than the impedance in response to the pacing amplitude capture threshold being less than the minimum voltage charge.

14. The ICD of claim 1, wherein the control module is further configured to enable a first pacing therapy comprising extra-cardiovascular pacing pulses delivered using the selected pacing output configuration and disabling a second pacing therapy comprising extra-cardiovascular pacing pulses from being delivered using the selected pacing output configuration.

15. The ICD of claim 14, wherein the first pacing therapy comprises at least one of anti-tachycardia pacing (ATP) therapy and/or asystole pacing therapy and the second pacing therapy comprises bradycardia pacing therapy.

16. The ICD of claim 1, wherein the control module is further configured to enable top-off charging of the high voltage capacitor in response to selecting the high voltage pacing output configuration.

17. The ICD of claim 1, wherein;
the low voltage charging circuit is configured to charge the plurality of low voltage capacitors up to a first maximum voltage; and
the high voltage therapy module is configured to charge the high voltage capacitor up to a second maximum voltage that is greater than the first maximum voltage.

18. The ICD of claim 17, wherein:
the high voltage charging circuit comprises a transformer for charging the high voltage capacitor up to the second maximum voltage; and
the low voltage therapy circuit is configured to charge the plurality of low voltage capacitors up to the first maximum voltage without a transformer.

19. A method performed by an extra-cardiovascular implantable cardioverter defibrillator (ICD) having a low voltage therapy module and a high voltage therapy module, the method comprising:
performing a pacing capture test;
based on the pacing capture test, selecting by a control module of the ICD a pacing output configuration from among at least a low-voltage, pacing output configuration of the low voltage therapy module and a high-voltage, pacing output configuration of the high voltage therapy module, the high voltage therapy module comprising a high voltage capacitor having a first capacitance and the low voltage therapy module comprising a plurality of low voltage capacitors each having up to a second capacitance that is less than the first capacitance; and
controlling a respective one of the low voltage therapy module and the high voltage therapy module to deliver extra-cardiovascular pacing pulses in the selected one of the low-voltage pacing output configuration and the high-voltage pacing output configuration via a plurality of extra-cardiovascular electrodes coupled to the ICD.

20. The method of claim 19, wherein:
performing the pacing capture test comprises:
controlling the low voltage therapy module to deliver at least one pacing pulse in a first low-voltage pacing output configuration;
determining that the at least one pacing pulse captures a patient's heart from a cardiac electrical signal received by a sensing module of the ICD via the extra-cardiovascular electrodes; and
determining that first pacing capture threshold criteria are met in response to determining if that the at least one pacing pulse captures the patient's heart; and
selecting the pacing output configuration comprises selecting the first low-voltage pacing output configuration in response to the first pacing capture threshold criteria being met.

* * * * *